(12) United States Patent
Petersen et al.

(10) Patent No.: US 10,717,957 B2
(45) Date of Patent: Jul. 21, 2020

(54) EMBRYO ASSESSMENT

(71) Applicant: UNISENSE FERTILITECH A/S, Aarhus N (DK)

(72) Inventors: Bjorn Molt Petersen, Viby J (DK); Mai Faurschou, Aarhus N (DK); Mikkel Boel, Aarhus V (DK)

(73) Assignee: UNISENSE FERTILITECH A/S (DK)

( * ) Notice: Subject to any disclaimer, the term of this patent is extended or adjusted under 35 U.S.C. 154(b) by 257 days.

(21) Appl. No.: 15/507,243

(22) PCT Filed: Oct. 2, 2015

(86) PCT No.: PCT/EP2015/072820
§ 371 (c)(1),
(2) Date: Feb. 27, 2017

(87) PCT Pub. No.: WO2016/050964
PCT Pub. Date: Apr. 7, 2016

(65) Prior Publication Data
US 2017/0283754 A1 Oct. 5, 2017

(30) Foreign Application Priority Data
Oct. 3, 2014 (GB) .................................. 1417553.3

(51) Int. Cl.
| C12M 1/36 | (2006.01) |
| C12M 3/00 | (2006.01) |
| C12M 1/34 | (2006.01) |
| G06K 9/00 | (2006.01) |
| G02B 21/00 | (2006.01) |
| G06K 9/62 | (2006.01) |
| G01N 21/01 | (2006.01) |

(52) U.S. Cl.
CPC .............. *C12M 1/36* (2013.01); *C12M 21/06* (2013.01); *C12M 41/36* (2013.01); *C12M 41/46* (2013.01); *C12M 41/48* (2013.01); *G02B 21/0084* (2013.01); *G06K 9/00147* (2013.01); *G06K 9/6201* (2013.01); *G06K 9/6209* (2013.01); *G01N 2021/0125* (2013.01); *G01N 2021/0137* (2013.01); *G06K 9/627* (2013.01); *G06K 9/6215* (2013.01)

(58) Field of Classification Search
None
See application file for complete search history.

(56) References Cited

U.S. PATENT DOCUMENTS

2013/0116499 A1 5/2013 Kkai et al.
2014/0220618 A1 8/2014 Wirka et al.

FOREIGN PATENT DOCUMENTS

| WO | 2012/163363 | 12/2012 |
| WO | 2013/004239 | 1/2013 |
| WO | 2014/033210 | 3/2014 |

OTHER PUBLICATIONS

International Search Report dated Dec. 21, 2015, issued in International Application No. PCT/EP2015/072820.
Written Opinion of the International Searching Authority dated Dec. 21, 2015, issued in International Application No. PCT/EP2015/072820.
Combined Search and Examination Report under Sections 17 and 18(3) dated Jun. 22, 2015, issued in GB Patent Application 1417553.3.
M. Meseguer et al: "The use of morphokinetics as a predictor of embryo implantation", Human Reproduction, vol. 26. No. 10, Aug. 9, 2011 (Aug. 9, 2011), pp. 2658-2671, XP55033123, ISSN: 0268-1161, DOI: 10.1093/humrep/der256 p. 2662. left-hand column, paragraph 6—right-hand column, paragraph 1; figure 6; tables I-II.
Irene Rubio et al: "Limited implantation success of direct-cleaved human zygotes: a time-lapse study", Fertility and Sterility. , vol. 98, No. 6, Dec. 1, 2012 (Dec. 1, 2012), pp. 1458-1463, XP055234657, USA ISSN: 0015-0282, DOI: 10.1016/j.fertnstert.2012.07.1135 p. 1459, left-hand column, paragraph 3 p. 1460, right-hand column, paragraph 2-5; figures 1-2; table 1.

(Continued)

*Primary Examiner* — Blaine Lankford
(74) *Attorney, Agent, or Firm* — Steptoe & Johnson LLP

(57) ABSTRACT

A method of ranking embryos to indicate their development potential. The method comprises: obtaining values for a plurality of characteristics relating to the morphological development of the embryos during an observation period; determining for respective ones of the embryos whether or not the embryo has undergone a direct cleavage event, and ranking the embryos determined to have undergone a direct cleavage event with a ranking that indicates a lower development potential than for the embryos not determined to have undergone a direct cleavage event; and for the embryos not determined to have undergone a direct cleavage event, determining whether or not a duration of a predefined developmental stage for the embryo exceeds a predefined threshold duration, and ranking embryos for which the duration of the predefined developmental stage is determined to exceed the predefined threshold duration with a ranking that indicates a lower development potential than for the embryos for which the duration of the predefined developmental stage is not determined to exceed the predefined threshold duration; and for the embryos for which the duration of the predefined developmental stage is not determined to exceed the predefined threshold duration, determining whether or not the relative durations of two predefined developmental stages for the embryo is outside a predefined range, and ranking embryos for which the relative durations of two predefined developmental stages for the embryo is outside a predefined range with a ranking that indicates a lower development potential than for the embryos for which the relative durations of two predefined developmental stages for the embryo is not outside the predefined range.

11 Claims, 13 Drawing Sheets

(56) References Cited

OTHER PUBLICATIONS

H. N. Ciray et al: "Proposed guidelines on the nomenclature and annotation of dynamic human embryo monitoring by a time-lapse user group", Human Reproduction, vol. 29. No. 12, Oct. 24, 2014 (Oct. 24, 2014), pp. 2650-2660, XP055234648, GB ISSN: 0268-1161, DOI: 10.1093/humrep/deu278 cited in the application p. 2656, left-hand column, paragraph 2—right-hand column, paragraph 1.

Kaser Daniel J et al: "Clinical outcomes following selection of human preimplantation embryos with time-lapse monitoring: a systematic review", Human Reproduction Update Nov.-Dec. 2011,, vol. 20, No. 5, Sep. 1,2014 (Sep. 1,2014), pp. 617-631, XP009184565, ISSN: 1460-2369 p. 619, right-hand column, paragraph 2—p. 625, paragraph 3; figure 2; tables I, II, III, IV abstract.

Notification Concerning Transmittal of International Preliminary Report on Patentability (Chapter I of the Patent Cooperation Treaty) dated Apr. 13, 2017, issued in International Application No. PCT/EP2015/072820.

EMBRYO ASSESSMENT

This application claims the benefit under 35 USC 371 to International Application No. PCT/EP2015/072820, filed Oct. 2, 2015, which claims priority to GB Patent Application No. 1417553.3, filed Oct. 3, 2014, each of which is incorporated by reference in its entirety.

BACKGROUND OF THE INVENTION

Certain embodiments of the present invention relate to methods and apparatus for assessing the developmental potential of embryos, and in particular to ranking/scoring embryos according to their developmental potential.

Infertility affects more than 80 million people worldwide. It is estimated that 10% of all couples experience primary or secondary infertility. In vitro fertilization (IVF) is an elective medical treatment that may provide a couple who has been otherwise unable to conceive a chance to establish a pregnancy and become parents. It is a process in which eggs (oocytes) are taken from a woman's ovaries and then fertilized with sperm in the laboratory. The embryos created in this process are then placed into the uterus for potential implantation. In between fertilization and transfer the embryos are typically stored in an incubation chamber of an incubator for 2-6 days during which time they may be regularly monitored, for example through imaging, to assess their development. Conditions within the incubator, such as temperature and atmospheric composition, are controlled, generally with a view to emulating the conditions in the oviduct and uterus.

In a typical IVF cycle a number of eggs from a single patient will be fertilized and the resulting embryos incubated. However, it is usual for not all incubated embryos to be transferred to the patient's uterus. This is to reduce the risk of potentially dangerous multiple births. Embryos will typically be selected for transfer on the basis of an assessment of the development potential of the embryos that have been incubated. Embryos determined to have the greatest potential for developing into a live birth will be preferentially selected over other embryos in their cohort. Accordingly, an important aspect of IVF treatment is assessing development potential of the embryos comprising a cohort, i.e. determining embryo quality where embryo quality is a prediction representing the likelihood of an embryo successfully implanting, developing in the uterus after transfer and leading to the birth of a healthy baby.

A powerful tool for assessing embryo quality that has developed over recent years is time-lapse embryo imaging. Time-lapse embryo imaging involves obtaining images of embryos during their development. This can allow the timings of various developmental events, such as cell divisions, and/or the presence or absence of other characteristics relating to the development of an embryo, for example in terms of cell-uniformity (evenness) at different stages, the appearance of pro-nuclei (PN), and the presence of multi-nucleation (MN), to be established.

These timings and characteristics may sometimes be referred to as morphokinetic/morphological parameters for the embryo. In this regard, the terms "morphokinetic" and "morphological" will generally be used herein interchangeably, although in some respects morphokinetic characteristics may strictly be considered a subset of morphological characteristics, namely those morphological characteristics specifically relating to timings. Studies have shown how the timings and durations of various embryonic development events and the presence or absence of various other development characteristics can be correlated with development potential for an embryo.

Models for embryo selection (i.e. models for assessing the developmental potential of an embryo) that take account of morphokinetic parameters can be constructed, evaluated and validated using Known Implantation Data (KID), whereby positive KID embryos are ones which are known to have subsequently implanted and negative KID embryos are ones which are known not to have subsequently implanted.

As an example of a simple model for assessing an embryo's development potential, a relatively early time of division from one cell to two cells has been found to be an indicator of a good quality embryo. Other morphokinetic parameters, for example the degree of synchronicity in the two divisions when dividing from two cells to four cells, are also found to be sensitive to embryo quality. More generally, there has been proposed various approaches for assessing the development potential of an embryo from parameters relating to the embryo's in-vitro development. Consequently, an aim of time-lapse imaging is to establish values for various parameters relating to the timings of various embryo development events and/or other characteristics relating to the development of the embryo, for example in terms of cell-uniformity (evenness) at different stages, the appearance of pro-nuclei (PN), and the presence of multi-nucleation (MN). Establishing values and characteristics relating to embryo development from a series of time-lapse images is sometimes called annotation.

While various timings and characteristics associated with embryo development have been found to help provide quality indicators for development of an embryo, the specific values for these which indicate a good quality embryo can be different for different embryos according to the conditions under which the embryo is incubated and the manner in which the various events are allocated. For example, one clinic might incubate embryos with a certain percentage oxygen atmosphere and temperature while another clinic might incubate embryos with a different percentage oxygen atmosphere and temperature. This can mean the optimum timing for a given morphological event in the development of an embryo may be different for the different clinics/incubator conditions.

FIG. 1 is a graph representing this principle (this graph is highly schematic and is not based on real data). Thus, FIG. 1 shows an example of how implantation likelihood, Imp %, might vary as a function of the timing of an arbitrary developmental event X (e.g. duration of a particular cell cycle or time of a particular cleavage). The solid curve represents the variation in implantation likelihood as a function of the observed timing for X for embryos developed according to a first set of conditions while the dashed curve represents the variation for embryos developed according to a second set of conditions. For example, the solid curve may represent embryos incubated in a relatively low oxygen atmosphere while the dashed curve may represent embryos incubated in a relatively high oxygen atmosphere. As another example, the solid curve might represent embryos that have been fertilised through intracytoplasmic sperm injection (ICSI) while the dashed curve might represent embryos that have been fertilised through in-vitro fertilisation (IVF). As yet another example, the two curves might represent embryos developed at different clinics. The two curves in FIG. 1 are systematically offset from one another because embryos incubated under different conditions will generally develop at different rates in at least some respects.

Accordingly, while FIG. 1 shows the time associated with the developmental event X can be used to identify embryos having relatively high implantation likelihood for embryos developed under both sets of conditions, the actual values of X associated with high implantation likelihood are different for the two groups. For example, for embryos incubated under the first set of conditions (solid line) an optimum range for the timing of X might be considered to be from h1 to h2, while an optimum range for embryos incubated under the second set of conditions (dashed line) might be considered to be from h3 to h4. What this means in practice is that different models for assessing the development potential of embryos will be needed for the different populations.

However, it would be preferable if a single model could be established that is applicable for embryos developed under various different conditions, i.e. what might be termed a universally-applicable model (or at least a model applicable to embryos developed under a range of different conditions). Not only would a universally-applicable model simplify the process of selecting a model to use for different embryo development conditions, in some cases there may not be sufficient KID data available for a given set of development conditions to allow a model for those specific conditions to be reliably established, for example in the case of a "new" clinic. One simple solution for providing a single model for the schematic situation represented in FIG. 1 would be to assume an optimum range for the timing of X of between h1 and h4 for all embryos. However, this would result in embryos from each population being wrongly classified as having high implantation likelihood, which of course is not a satisfactory solution.

Accordingly, there is a desire to develop models for assessing the development potential (viability/quality) of embryos, such as an in-vitro incubating human embryos, which are applicable for embryos developed under a range of different conditions.

SUMMARY OF THE INVENTION

According to a first aspect of the invention there is provided a method of ranking embryos to indicate their development potential; the method comprising: obtaining values for a plurality of characteristics relating to the morphological development of the embryos during an observation period; determining for respective ones of the embryos a measure of whether or not the embryo has undergone a direct cleavage event, and ranking the embryos determined to have undergone a direct cleavage event with a ranking that indicates a lower development potential than for the embryos not determined to have undergone a direct cleavage event; and for the embryos not determined to have undergone a direct cleavage event, determining whether or not a measure of a duration of a predefined developmental stage for the embryo exceeds a predefined threshold duration, and ranking embryos for which the duration of the predefined developmental stage is determined to exceed the predefined threshold duration with a ranking that indicates a lower development potential than for the embryos for which the duration of the predefined developmental stage is not determined to exceed the predefined threshold duration; and for the embryos for which the duration of the predefined developmental stage is not determined to exceed the predefined threshold duration, determining whether or not a measure of a relative duration of a first predefined developmental stage for the embryo with respect to a second predefined developmental stage for the embryo is outside a predefined range, and ranking embryos for which the relative duration is outside the predefined range with a ranking that indicates a lower development potential than for the embryos for which the relative duration of is not outside the predefined range.

According to a second aspect of the invention there is provided an apparatus for ranking embryos to indicate their development potential, the apparatus comprising: a data input element configured to obtain values for a plurality of characteristics relating to the morphological development of the embryos during an observation period; and a processor element configured to: determine for respective ones of the embryos a measure of whether or not the embryo has undergone a direct cleavage event, and ranking the embryos determined to have undergone a direct cleavage event with a ranking that indicates a lower development potential than for the embryos not determined to have undergone a direct cleavage event; and for the embryos not determined to have undergone a direct cleavage event, determine whether or not a measure of a duration of a predefined developmental stage for the embryo exceeds a predefined threshold duration, and ranking embryos for which the duration of the predefined developmental stage is determined to exceed the predefined threshold duration with a ranking that indicates a lower development potential than for the embryos for which the duration of the predefined developmental stage is not determined to exceed the predefined threshold duration; and for the embryos for which the duration of the predefined developmental stage is not determined to exceed the predefined threshold duration, determine whether or not a measure of a relative duration of a first predefined developmental stage for the embryo with respect to a second predefined developmental stage for the embryo is outside a predefined range, and ranking embryos for which the relative duration is outside the predefined range with a ranking that indicates a lower development potential than for the embryos for which the relative duration of is not outside the predefined range.

Other aspects of the invention include a non-transitory computer program product bearing machine readable instructions for carrying out the method of the first aspect of the invention and an apparatus loaded with and operable to execute machine readable instructions for carrying out the method of the first aspect of the invention.

Further aspects and features of the invention are defined by the claims.

It will be appreciated that features and aspects of the invention described herein in relation to the first and other aspects of the invention are equally applicable to, and may be combined with, embodiments of the invention according to other aspects of the invention as appropriate, and not just in the specific combinations described above.

It will be appreciated that features and aspects of the invention described above in relation to the first and other aspects of the invention are equally applicable to, and may be combined with, embodiments of the invention according to other aspects of the invention as appropriate, and not just in the specific combinations described above.

BRIEF DESCRIPTION OF THE DRAWINGS

The invention is now described by way of example only with reference to the following drawings in which.

DETAILED DESCRIPTION

Figure 1:
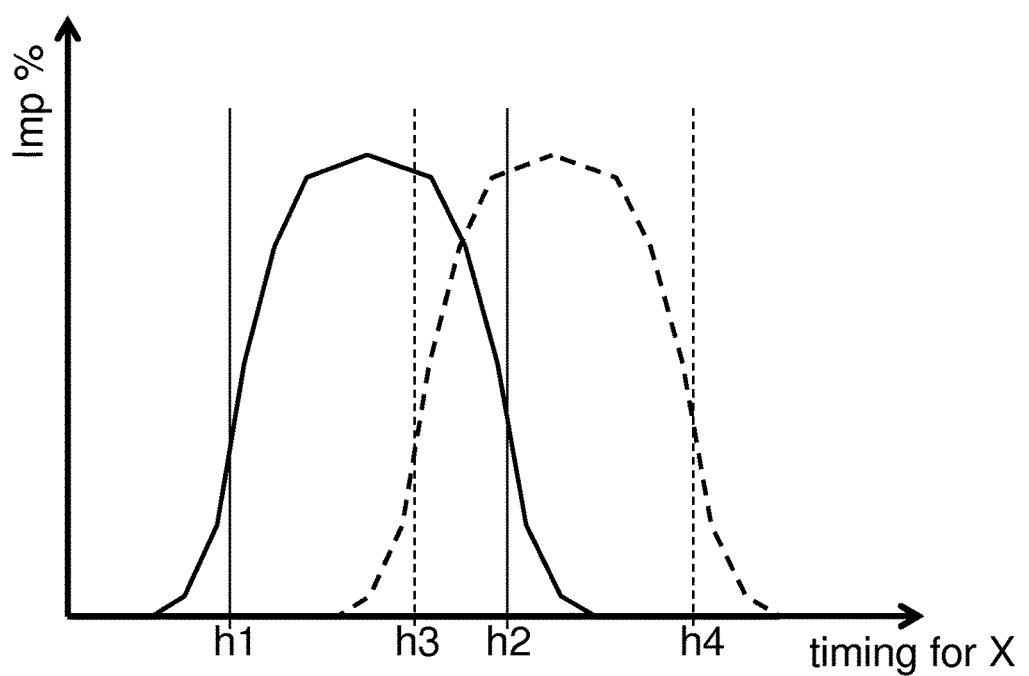
FIG. 1 is a highly schematic plot representing how implantation likelihood might vary as a function of timing associated with an arbitrary developmental event for two populations of embryos incubated under two different sets of conditions.

Aspects and features of certain examples and embodiments of the present invention are discussed/described herein. Some aspects and features of certain examples and embodiments may be implemented conventionally and these are not discussed/described in detail in the interests of brevity. It will thus be appreciated that aspects and features of apparatus and methods discussed herein which are not described in detail may be implemented in accordance with any conventional techniques for implementing such aspects and features.

Unless the context demands otherwise, the terms used herein should be interpreted in accordance with their meanings as commonly understood by one of ordinary skill in the art to which this disclosure belongs. Some terms may be used herein in accordance with the following definitions (unless the context demands another meaning).

Cleavage time (cell division time) is defined as the first observed timepoint relative to a defined start point (zero time) when newly formed blastomeres are completely separated by confluent cell membranes, the cleavage time is therefore the time of completion of a blastomere cleavage. Cleavage times may thus be defined as follows:

t2: Time of cleavage to 2 blastomere embryo
t3: Time of cleavage to 3 blastomere embryo
t4: Time of cleavage to 4 blastomere embryo
t5: Time of cleavage to 5 blastomere embryo
t6: Time of cleavage to 6 blastomere embryo
t7: Time of cleavage to 7 blastomere embryo
t8: Time of cleavage to 8 blastomere embryo
tn: Time of cleavage to n blastomere embryo It will be appreciated cleavage time may equally be defined with respect to other time points associated with cell division. For example, in the above definition the cleavage time is related to a time associated with the completion of cell division (i.e. when newly formed blastomeres are completely separated), but in another implementation, the time of cleavage may equally be defined as a time associated with the beginning of cell division, or a time associated with a midway point for cell division.

In the present context the cleavage times are usually expressed as hours post a defined zero time. The zero time may be the time of insemination (e.g. the time of IntraCytoplasmic Sperm Injection (ICSI), also called microinjection), or it could also be post the time of mixing of sperm and oocyte (in traditional IVF) or post the time where the successful fusion of gametes to form a new organism (the zygote) is observed for the first time, i.e. exclusion of the second polar body. Similarly, it could be post the time for pronuclear appearance or fading/disappearance or other significant developmental parameter. With regard to pronuclear fading/disappearance, the terms "faded" and "disappeared" in relation to the pro-nuclei (PN) may be used herein interchangeably. The term tPNf may be used to indicate a determined time for pro-nuclei fading (i.e. a time point determined to be the time at which the pro-nuclei (PN) are no longer apparent).

The first cell cycle duration cc1 is the period between fertilization and the cleavage time t2 that provides the first pair of daughter cells (i.e. the first second-generation cells). The second cell cycle duration cc2 is the period between the cleavage time t2 that provides the first pair of daughter cells and the cleavage time t3 that provides the first pair of granddaughter cells (i.e. the first third-generation cells). The third cell cycle duration cc3 is the period between the cleavage time t3 that provides the first pair of granddaughter cells and the cleavage time t5 that provides the first pair of great-granddaughter cells (i.e. the first fourth-generation cells). The fourth cell cycle duration cc4 is the period between the cleavage time t5 that provides the first pair of great-granddaughter cells and the cleavage time t9 that provides the first pair of great-great-granddaughter cells (i.e. the first fifth-generation cells).

These cell cycle durations are thus based on the fastest of the blastomeres to divide for each new generation. However, there are additional cell cycle durations associated with division of slower blastomeres.

For example, in addition to cell cycle duration cc2 there is a cell cycle duration cc2b corresponding to the period between the cleavage time t2 that provides the first pair of daughter cells and the cleavage time t4 that provides the second pair of granddaughter cells. In this regard cell cycle duration cc2 may also be referred to as cell cycle duration cc2a for simplicity in terminology.

Furthermore, in addition to cell cycle duration cc3 there is a cell cycle duration cc3b corresponding to the period between the cleavage time t3 that provides the first pair of granddaughter cells and the cleavage time t6 that provides the second pair of great-granddaughter cells. There is also a cell cycle duration cc3c corresponding to the period between the cleavage time t4 that provides the second pair of granddaughter cells and the cleavage time t7 that provides the third pair of great-granddaughter cells. There is also a cell cycle duration cc3d corresponding to the period between the cleavage time t4 that provides the second pair of granddaughter cells and the cleavage time t8 that provides the fourth pair of great-granddaughter cells. In this regard cell cycle duration cc3 may also be referred to as cell cycle duration cc3a for consistency in terminology.

Thus, duration of cell cycles is defined as follows:

cc1=t2: First cell cycle.

cc2 (also referred to cc2a)=t3−t2: Second cell cycle, duration of period as 2 blastomere embryo.

cc2b=t4−t2: Second cell cycle for both blastomeres, duration of period as 2 and 3 blastomere embryo.

cc3 (also referred to cc3a)=t5−t3: Third cell cycle, duration of period as 3 and 4 blastomere embryo.

cc3b, cc3c, cc3d=t6−t3; t7−t4; and t8−t4 respectively: Third cell cycle for slower blastomeres, duration of period as a 3, 4, and 5 blastomere embryo; as a 4, 5 and 6 blastomere embryo, and as a 4, 5, 6 and 7 blastomere embryo respectively.

cc2_3=t5−t2: Second and third cell cycle, duration of period as 2, 3 and 4 blastomere embryo (i.e. cc2+cc3).

cc4=t9−t5: Fourth cell cycle, duration of period as 5, 6, 7 and 8 blastomere embryo.

Synchronicities are defined as follows:

s2=t4−t3: Synchrony in division from 2 blastomere embryo to 4 blastomere embryo.

s3=t8−t5: Synchrony in division from 4 blastomere embryo to 8 blastomere embryo.

s3a=t6−t5; s3b=t7−t6; s3c=t8−t7: Duration of the individual cell divisions involved in the development from 4 blastomere embryo to 8 blastomere embryo.

Figure 2:
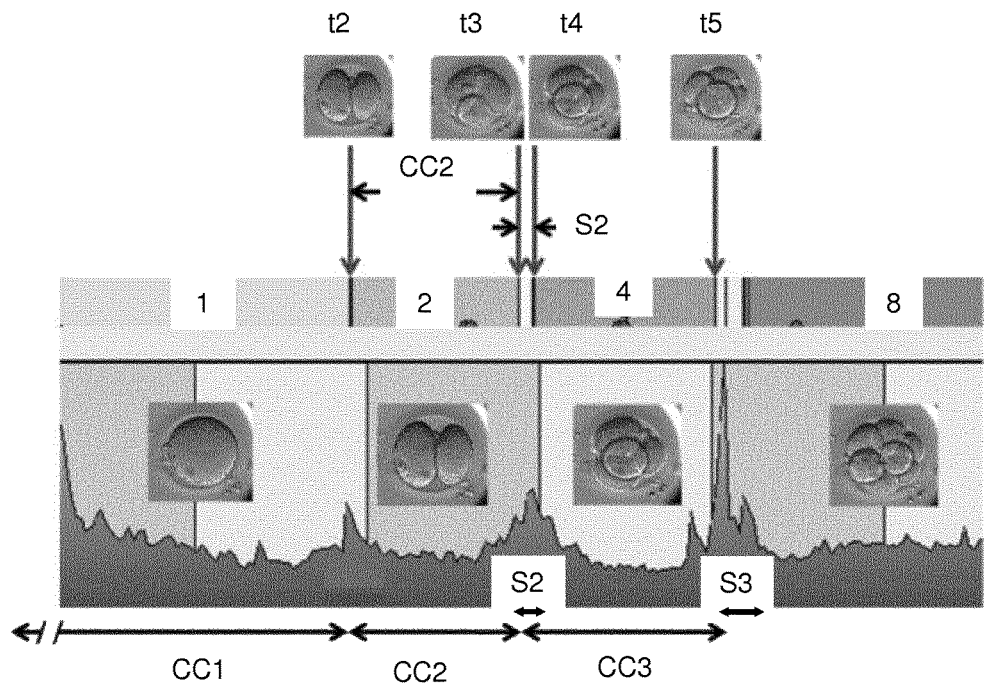
FIG. 2 schematically represents some nomenclature as used herein for an embryo cleavage pattern showing cleavage times (t2 to t5), duration of cell cycles (cc1 to cc3), and synchronies (s2 and s3) in relation to images obtained.
Figure 3:
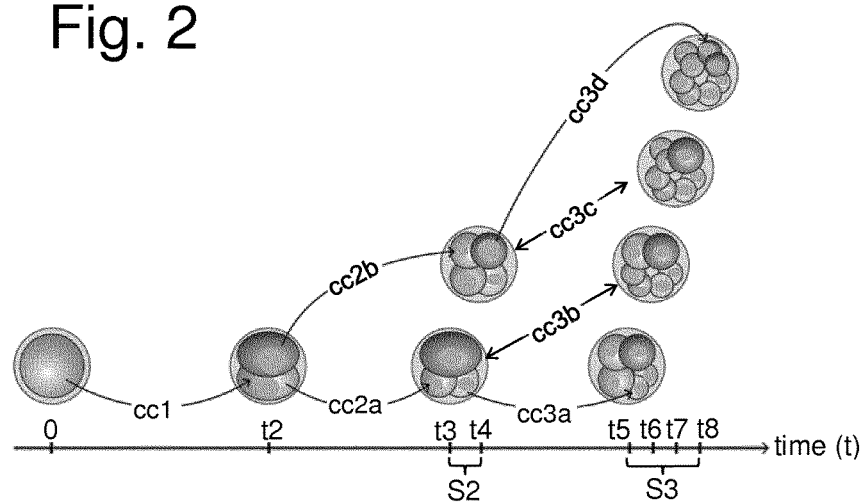
FIG. 3 schematically represents an embryo at different embryo developmental events from initial insemination (at time t=0) and at cleavage times t2-t8 with some associated aspects of timing terminology as used herein.

FIGS. 2 and 3 schematically represent some aspects of the terminology used herein regarding the timings and durations of some embryo developmental events such as discussed above. FIG. 2 shows a number of images of an embryo at various stages of development and indicates various timings associated with various developmental events, such as t2, t3, t4, t5, cc1, cc2 (which may also be referred to herein as cc2a), cc3 (which may also be referred to herein as cc3a), s2 and s3. FIG. 3 schematically represents from left to right the development of the embryo through the one, two, three, four, five, six, seven and eight blastomere stages. The times t2 to t8 at which the respective cell division stage are complete is schematically marked along the bottom axis. FIG. 3 also schematically indicates the cell cycle durations cc1, cc2a, cc2b, cc3a, cc3b, cc3c and cc3d and synchronicities S2 and S3.

Cleavage period is defined as the period of time from the first observation of indentations in the cell membrane (indicating onset of cytoplasmic cleavage) to when the cytoplasmic cell cleavage is complete so that the blastomeres are completely separated by confluent cell membranes. Also termed as duration of cytokinesis.

Fertilization and cleavage may in some respects be considered to be the primary morphological/morphokinetic events of an embryo, at least until the 8 blastomere stage or until the start of compaction. Cleavage time, cell cycle, synchrony of division and cleavage period are examples of morphological embryo parameters that can be defined from these primary morphological events and each of these morphological embryo parameters may be defined as the duration of a time period between two morphological events, e.g. measured in hours.

Direct cleavage is when a cell divides more quickly than the time which is assumed to be required for its DNA to properly replicate before division. For example, a cell may divide into two daughters cells, and then if one of the daughter cells divides in two granddaughter cells before the time normally taken to replicate its DNA, it may be assumed the initial cell has undergone a direct cleavage event. That is to say the initial cell has, within a predefined time period, divided from one cell to more than two cells, e.g. three cells. Direct cleavage may occur in different cell cycles. For example, referring to FIG. 3, a short period for any of cc2a, cc2b, cc3a, cc3b, cc3c, cc3d may be taken to be indicative of a direct cleavage event.

As already mentioned, it is known to establish a measure of a development potential for an embryo from various parameters associated with its development, such as parameters corresponding to (or based on) the timings discussed above, and in order to do this, values for the relevant parameters of interest may be determined from time-lapse images of the embryo as it develops through the relevant stages. In some approaches for determining a development potential for an embryo other developmental characteristics may be of interest. For example, an assessment of the quality of an embryo may take account of values established for the following morphological characteristics:

NOT2PN: Indication of whether or not two pro-nuclei are properly identified for the embryo. This characteristic may be determined visually from an image of the embryo at the appropriate develop the site with a mental stage and may, for example take a simple binary value to indicate whether or not to pro-nuclei are properly identified the embryo, or might take a value which indicates the number of targeted identified for the embryo, for example a value corresponding to "0", "1", "2", "3", or "4 or more" according to the number of pro-nuclei identified for the embryo (a value of "2" is normal).

MN2: Indication of (any) multi-nucleation observed at the two blastomere (cell) stage. This characteristic may be determined visually from an image of the embryo at the appropriate developmental stage and may take values corresponding to "0", "1" or "2" corresponding to the number of cells determined to show multi-nucleation at the two blastomere stage.

MN4: Indication of (any) multi-nucleation observed at the four blastomere stage. This characteristic may be determined visually from an image of the embryo at the appropriate developmental stage and may take values corresponding to "0", "1", "2", "3" or "4" corresponding to the number of cells identified as showing multi-nucleation at the four blastomere stage.

UNEVEN2: Indication of (un)evenness of the blastomeres at the two blastomere stage. This characteristic may be determined visually from an image of the embryo at the appropriate developmental stage and may take values corresponding to "Even" (blastomeres in the two blastomere embryo are classified as being even) or "Uneven" (blastomeres in the two blastomere embryo are classified as being uneven).

UNEVEN4: Indication of (un)evenness of the blastomeres at the four blastomere stage. This characteristic may be determined visually from an image of the embryo at the appropriate developmental stage and may take values corresponding to "Even" (blastomeres in the four blastomere embryo are classified as being even) or "Uneven" (blastomeres in the four blastomere embryo are classified as being uneven).

It will be appreciated that the establishment of values for some of these parameters can include an element of subjectivity, for example in respect of whether cells comprising an embryo are even or are not even. It will also be appreciated the terminology adopted for the specific values (e.g. "even", "uneven") is not significant, and the values could equally be characterized in other ways, e.g. as "true" or "false" of by numerical values associated with the different potential states, e.g. "0" for even, "1" for uneven).

It will further be appreciated that the above-identified timings and characteristics associated with embryo development are set out to provide an overall understanding of the types of parameters and characteristics that may be of interest when seeking to provide models for assessing the development potential of embryos and typically it will only be a subset of these parameters and/or characteristics which is of interest for a given model.

Embryo quality is a measure of the ability of an embryo to successfully implant and develop in the uterus after transfer. Embryos of high quality have a higher probability of successfully implanting (high implantation likelihood) and developing in the uterus to a healthy baby after transfer than low quality embryos. However, even a high quality embryo is not a guarantee for implantation as the actual transfer and the woman's receptivity influences the final result.

Viability and quality may be used interchangeably. Embryo quality (or viability) measurement is a parameter intended to reflect the quality (or viability) of an embryo such that embryos with certain values of the quality parameter (e.g. high or low values depending on how the parameter is defined) have a high probability of being of high quality (or viability), and low probability of being low quality (or viability). Whereas embryos with certain other values for the quality (or viability) parameter have a low probability of having a high quality (or viability) and a high probability of being low quality (or viability)

The term "developmental potential" may be used to reflect an estimated likelihood of an embryo to develop to blastocyst stage, to implant, to result in pregnancy, to develop to a stage associated with a heartbeat and/or to result in a live-born baby. In some embodiments the development potential may be a determination of embryo quality. Developmental potential may be equated with embryo quality. An embryo having a positive developmental potential (i.e. a good (high) embryo quality) is one that is more likely develop to blastocyst stage and/or result in successful implantation and/or develop in the embryo in the uterus after transfer and/or result in pregnancy and/or result in a live-born baby as compared to an embryo having a negative developmental potential (or poor (low) embryo quality).

Thus embryos determined to be of good (high) quality are determined to have a higher probability of successfully implanting and/or of developing in the uterus after transfer compared with low quality embryos. However, it will be appreciated a high quality embryo is not a guarantee for implantation as the actual transfer and the woman's receptivity highly influences the final result.

In some cases the term "embryo" may be used to describe a fertilized oocyte after implantation in the uterus until 8 weeks after fertilization, at which stage it become a fetus. According to this definition the fertilized oocyte is often called a pre-embryo or zygote until implantation occurs. However, the term "embryo" as used herein will have a broader definition, which includes the pre-embryo phase. The term "embryo" as used herein encompasses all developmental stages from the fertilization of the oocyte through morula, blastocyst stages, hatching and implantation. Accordingly, the term embryo may be herein to denote each of the stages fertilized oocyte, zygote, 2-cell, 4-cell, 8-cell, 16-cell, compaction, morula, blastocyst, expanded blastocyst and hatched blastocyst, as well as all stages in between (e.g. 3-cell or 5-cell).

An embryo is approximately spherical and is composed of one or more cells (blastomeres) surrounded by a gelatine-like shell, the a cellular matrix known as the zona pellucida. The zona pellucida performs a variety of functions until the embryo hatches, and is a good landmark for embryo evaluation. The zona pellucida is spherical and translucent, and should be clearly distinguishable from cellular debris.

An embryo is formed when an oocyte is fertilized by fusion or injection of a sperm cell (spermatozoa). The term embryo is traditionally used also after hatching (i.e. rupture of zona pellucida) and the ensuing implantation. For humans the fertilized oocyte is traditionally called a zygote or an embryo for the first 8 weeks. After that (i.e. after eight weeks and when all major organs have been formed) it is called a fetus. However the distinction between zygote, embryo and fetus is not generally well defined. The terms embryo and zygote may be used herein interchangeably.

An embryo that is assessed in accordance with embodiments of the invention such as described herein may be previously frozen, e.g. embryos cryopreserved immediately after fertilization (e.g. at the 1-cell stage) and then thawed. Alternatively, they may be freshly prepared, e.g. embryos that are freshly prepared from oocytes by IVF or ICSI techniques for example. It will be appreciated that in so far as an embryo's development has been halted by freezing, the timings of developmental events after fertilization may be defined by ignoring the time between freezing and thawing. Alternatively, a starting time may be defined as one of the first developmental events, such as exclusion of second polarbody or appearance/disappearance of pronuclei, post thawing.

Fertilization may be considered to be the time point where the sperm cell is recognized and accepted by the oocyte. The sperm cell triggers egg activation after the meiotic cycle of the oocyte has been suspended in metaphase of the second meiotic division. This results in the production and extrusion of the second polar body. Some hours after fusion of sperm and ovum, DNA synthesis begins. Male and female pronuclei (PN) appear. The PN move to the center of the egg and the membranes breakdown and the PN disappear (fade). This combination of the two genomes is called syngamy. Hereafter, the cell divisions begin.

The time when the pronuclei disappear may be referred to as tPNf. The terms "fade(d)" and "disappear(ed)" in relation to the pro-nuclei (PN) may be used herein interchangeably. During embryonic development, blastomere numbers increase geometrically (1-2-4-8-16- etc.). Synchronous cell cleavage is generally maintained to the 8-cell stage or later, until compaction in human embryos. After that, cell cleavage becomes asynchronous and finally individual cells possess their own cell cycle. Human embryos produced during infertility treatment can be transferred to the recipient before 8-blastomere stage. In some cases human embryos are also cultivated to the blastocyst stage before transfer. This is preferably done when many good quality embryos are available or prolonged incubation is necessary to await the result of a pre-implantation genetic diagnosis (PGD). However, there is a tendency towards prolonged incubation as incubation technology improves.

Some example implementations of embodiments of the invention may be used to establish blastocyst related parameters.

A blastocyst quality criterion/measure is an example of an embryo quality criterion/measure. The blastocyst quality criteria may, for example, relate to the development of the embryo from compaction, i.e. initial compaction, to the hatched blastocyst. Compaction is a process wherein an intensification of the contacts between the blastomeres with tight junction and desmosomes result in reduction of the intercellular space and a blurring of the cell contours. Before compaction the blastomeres of the embryo can be followed individually and before compaction the embryo development follows a route of distinct and mostly synchronous cell divisions that can be observed and readily annotated. After compaction the embryo development is characterized by a more or less continuous development from morula to blastocyst, where individual blastomeres become difficult to track, but a number of stages may nonetheless be characterised by establishing values for parameters associated with these stages by visual inspection of images obtained for the relevant development stages.

Start of compaction (SC) describes the first time a compaction between two or more blastomeres is observed. Thus, SC marks the initiation of the compaction process.

Morula (M) is associated with the first time where no plasma-membranes between blastomeres are visible. When the compaction process is complete no plasma-membranes between any of the blastomeres forming the compaction are visible and the embryo can be defined as a morula. Most often Morula is seen after the third synchrony period S3 (i.e. after t8) close to, or right in the beginning, of the fourth synchrony period S4 (i.e. at t9), but may be earlier. Rarely do embryos cleave to 16 cells or more before compaction is initiated in human embryos.

Initial differentiation of trophectoderm (IDT) is defined as the first time where distinct trophectoderm cells are recognized. Start of blastulation (SB) is defined as the first time a fluid-filled cavity, the blastocoel, can be observed. It is also referred to as "Onset of cavitation". It describes the initiation of the transition period between the morula stage and the blastocyst stage of the embryo. Embryos often remain in this transition stage for a period of time before entering the actual blastocyst stage. The onset of cavitation usually appears immediately after differentiation of the trophectoderm cells. The outer layer of the morula with contact to the outside environment begins to actively pump salt and water into the intercellular space, as a result of which a cavity (the blastocoel) begins to form.

Initial differentiation of inner cell mass (IDIOM) defined as the first time the inner cell mass can be recognized. IDIOM describes the initiation of inner cell mass development. An eccentrically placed cluster of cell connected of gab junction where the boundaries between the cells seem not well defined.

Blastocyst (B) may be defined as the last image before the blastocyst begins to expand. When this take place, the zona pellucid usually starts to change and there is a clear distinction between trophectoderm and inner cell mass cells.

Onset of expansion of the blastocyst (EB) may be defined as the first time the embryo has filled out the periviteline space and starts moving/expanding Zona Pelucidae. EB may describe the initiation of the embryo's expansion. As the blastocyst expands the zona pellucida becomes visibly thinner.

Hatching blastocyst (HB) may be defined as the first time a trophectoderm cell has escaped/penetrated the zona pellucida or a certain fraction have hatched.

Fully hatched blastocyst (FH) is defined as when hatching is completed with shedding zona pellucida.

Various timings associated with blastocyst development may be defined as follows:

tM=Time from insemination to formation of morula (hours)

tSB=Time from insemination to start of blastulation (hours)

tB=Time from insemination to formation of blastocyst (hours)

tEB=Time from insemination to formation of expanded blastocyst (hours)

tHB=Time from insemination to hatching blastocyst (hours)

Figure 4:
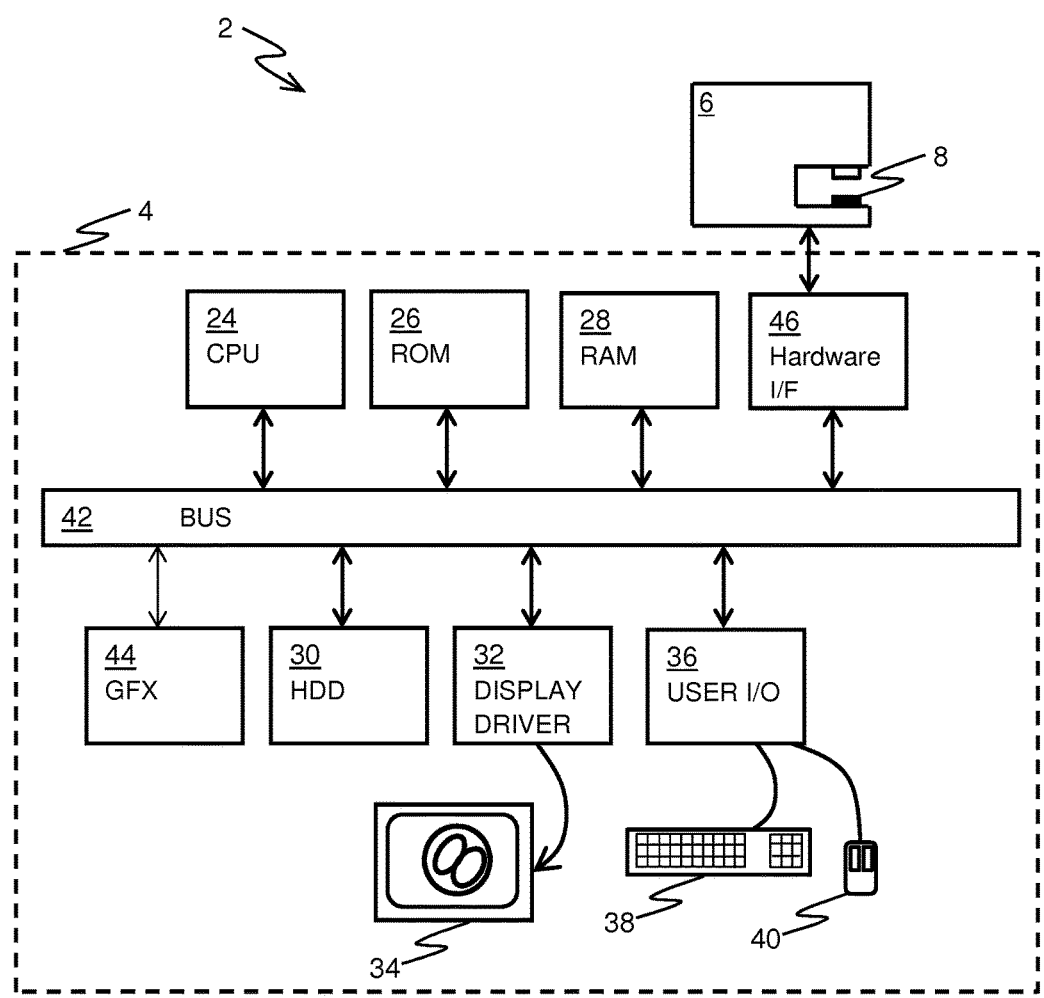
FIG. 4 schematically represents an apparatus for determining a development potential for an embryo in accordance with an embodiment of the invention.

FIG. 4 schematically represents an apparatus 2 for determining a development potential for an embryo 8 in accordance with certain embodiments of the invention. The apparatus 2 comprises a general purpose computer 4 coupled to an embryo imaging system 6. The embryo imaging system 6 may be generally conventional and is configured to obtain images of the embryo 8 at various stages of development in accordance with established techniques. It will be appreciated that in general the embryo imaging system 6 will typically be configured to obtain images of a plurality of embryos, rather than just a single embryo, over a monitoring period. For example, a typical study may involve the analysis of a number of embryos, for example 72 embryos. The embryo imaging system may be configured to record images of each embryo (potentially with images of being taken in multiple focal planes) one at a time before moving on to image the next embryo. Once all embryos have been imaged, which might, for example, take 5 minutes, the cycle of imaging the individual embryos may be repeated to provide respective images for the respective embryos for the next time point.

The general purpose computer 4 is adapted (programmed) to execute a method for determining/assessing a development potential of an embryo from an analysis of images obtained from the embryo imaging system 6 as described further below.

Thus the computer system 4 is configured to perform processing of embryo image data in accordance with an embodiment of the invention. The computer 4 includes a central processing unit (CPU) 24, a read only memory (ROM) 26, a random access memory (RAM) 28, a hard disk drive 30, a hardware interface 46, a display driver 32 and display 34 and a user input/output (IO) circuit 36 with a keyboard 38 and mouse 40. These devices are connected via a common bus 42. The computer 4 also includes a graphics card 44 connected via the common bus 42. The graphics card includes a graphics processing unit (GPU) and random access memory tightly coupled to the GPU (GPU memory). The embryo imaging system 6 is communicatively coupled to the computer 4 via the hardware interface 46 in accordance with conventional technical techniques.

The CPU 24 may execute program instructions stored within the ROM 26, the RAM 28 or the hard disk drive 30 to carry out processing of embryo image data that may be stored within the RAM 28 or the hard disk drive 30. The RAM 28 and hard disk drive 30 are collectively referred to as the system memory. In some implementations, processing in accordance with embodiments of the invention may be based on embryo images obtained by the computer 4 directly from the imaging system 6. In other implementations, processing in accordance with embodiments of the invention may be based on embryo images previously obtained and stored in a memory of the computer 4, e.g. in RAM 28 of HDD 30 (i.e. the embryo imaging system 6 itself is not a required element of embodiments of the invention). Aspects of the computer 4 may largely be conventional except that the CPU is configured to run a program, which may for example be stored in RAM 28, ROM 26 or HDD 30, to perform processing in accordance with certain embodiments of the invention as described herein.

The embryo 8 in accordance with certain example implementations is monitored regularly using the embryo imaging system 6 to obtain the relevant information (i.e. timings associated with particular embryo developmental events, (non-)occurrence of particular embryo developmental characteristics). The embryo is preferably monitored at least once per hour, such as at least twice per hour, such as at least three times per hour, such as at least four times per hour, such as at least six times per hour, such as at least 12 times per hour. The monitoring is preferably conducted while the embryo is situated in an incubator used for culturing the embryo. This is preferably carried out through image acquisition of the embryo, such as discussed herein in relation to time-lapse methods.

Figure 5:
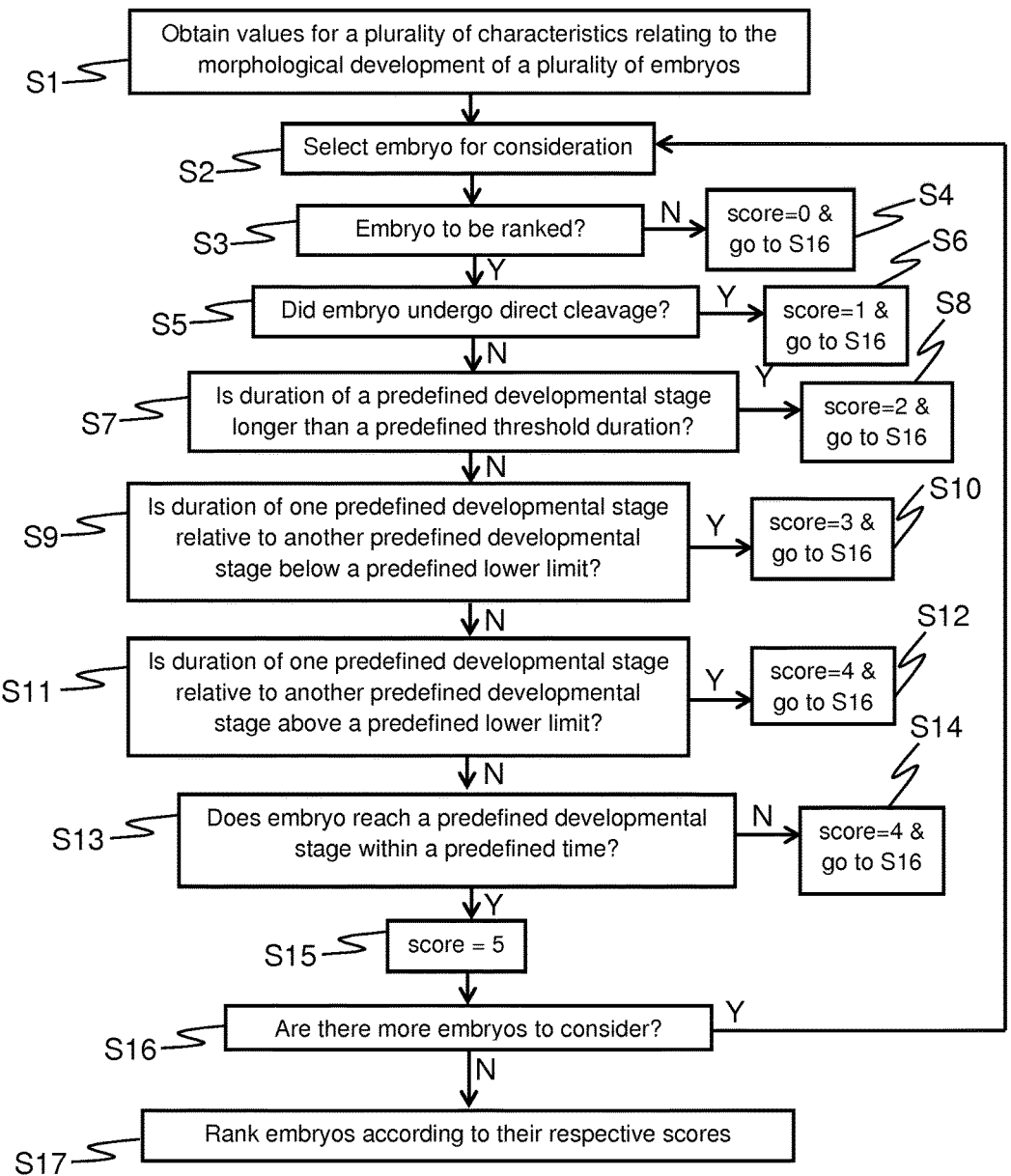
FIG. 5 is a flow diagram schematically representing a method of ranking embryos based on their development potential in accordance with some embodiments of the invention.

FIG. 5 is a flow diagram schematically representing a method for ranking embryos according to their development potential in accordance with certain embodiments of the invention. The method may be applied, for example, for ranking a plurality of embryos associated with a single patient to help identify which of the embryos are most likely to successfully implant/leads to a live birth. The number of embryos will of course vary between patients and treatment cycles, but in a typical case the plurality of embryos from a single patient in a single treatment cycle might be somewhere between 6 and 12 embryos, for example. The method may be a computer-implement method which may be implemented using the computer 4 of FIG. 4 with the CPU 24 implementing the method in accordance with a loaded program.

In step S1 a plurality of values for characteristics relating to the morphological development of the embryos during an observation period are obtained. In an approach for ranking embryos in the context of assessing embryos for their relevant development potential for a day three transfer, this observation period may, for example extend to around 72 hours, or more, after the relevant reference time (time zero). The morphological characteristics of interest will depend on the specific application at hand since different embodiments may rely on different morphological characteristics, as discussed further below. In this example it is assumed the characteristics obtained for each embryo are:

(i) an indication as to whether or not the embryo properly displays two pro-nuclei (e.g. a value for NOT2PN as defined above).

(ii) values for t3 and tPNf (a relatively small difference between these values being taken to be an indicator of the occurrence of direct cleavage)

(iii) the duration of a predefined developmental stage that is used here to identify whether the embryo's development is undesirably slow (in this example the development stage is from zero time (e.g. time of ICSI microinjection) to t3)

(iv) the durations of two predefined developmental stages which are used here to identify whether the relative duration of one of these developmental stages to the other is within a desired range (in this example the two developmental stages are the duration of cc3a (i.e. t5−t3) and the combined duration of cc2a and cc3a (i.e. t5−t2)).

(v) an indication as to whether the number of cells in the embryo failed to reach a given number within a given time (which in in this particular example is eight cells within 66 hours).

Thus, to summarise, values for the following characteristics relating to the morphological development of the embryos may be sought for each embryo in accordance with one example implementation of the method of FIG. 5: NOT2PN; tPNf; t2; t3; t5 and t8. It will be appreciated it may not be possible to obtain values for all these characteristics for all embryos. For example, it may be that an embryo does not reach the 8-cell stage within the observation period, in which case it would not be possible to obtain a value for t8 (corresponding to a determination that the embryo did not reach 8 cells within the observation/monitoring period).

Values for these parameters may be obtained in accordance with conventional techniques, for example using conventional time-lapse imaging of embryos in an incubator to obtain a series of images of the developing embryos, and using conventional annotation procedures for identifying the timings and occurrences of the various relevant morphological events from the series of images. For example, the values for these parameters may be obtained using an EmbryoScope® device for time-lapse monitoring of embryos during incubation and its associated EmbryoViewer® software for annotating the events of interest. The EmbryoScope® device and EmbryoViewer® software have been developed by, and are available from, Unisense FertiliTech NS (Aarhus, Denmark). It will be appreciated that in accordance with previously established techniques, annotation may be performed manually (e.g. based on user input) and/or automatically (e.g. based on numerical image analysis/processing) and/or semi-automatically (e.g. based on a mixture of numerical image processing and user input).

In step S2 one of the embryos is selected for consideration. In general, the approach of FIG. 5 is to sequentially establish a score for each embryo and the score may then be used as a basis for ranking the embryos according to their development potential. The order in which the embryos are considered is not significant, and in this regard the embryo that is selected in step S2 may be chosen arbitrarily from the embryos which remain to be scored. The selected embryo for a given iteration may be referred to as the current embryo for that iteration.

In step S3 a determination is made as to whether the current embryo should be ranked. In this example this is based on the value for NOT2PN. In some respects this may be seen as an initial screening step in which embryos having one or more characteristics which is known to be strongly associated with low development potential are identified.

If it is determined in Step S3 that the current embryo does not properly display two pro-nuclei, it is determined the embryo should not be ranked further and processing follows the branch marked N to step S4 in which the current embryo is attributed a score of 0, and processing then proceeds to step S16. In step S16 it is determined whether all the plurality of embryos have been considered or if there are more embryos to consider. If there are more embryos to consider, processing follows the branch marked Y backs to step S2 when the next embryo for consideration is selected.

If, on the other hand, it is determined in step S3 that the embryo does properly display two pro-nuclei, processing follows the branch marked Y to step S5.

In step S5 an assessment is made as to whether the embryo underwent direct cleavage during the observation period (direct cleavage has been found to be associated with relatively low development potential). In this example this is based on determining whether a time period associated with the embryo's development is less than a threshold duration, and if so, determining that the embryo has undergone a direct cleavage event. In this example implementation a direct cleavage event is deemed to have occurred if a measure of the time between tPNF and t3 (t3−tPNf)) is less than around 11.5 hours (e.g. less than 11.48 hours). Other threshold values could be used, for example the threshold value may be selected from the group comprising: 5 hours, 6 hours, 7 hours, 8 hours, 9 hours, 10 hours, 11 hours, 12 hours, 13 hours and 14 hours.

In some other example implementations different time periods may be used to identify whether there has been a direct cleavage event. For example, a direct cleavage event may be deemed to have occurred if a measure of the period (t3–t2) is less than a threshold amount, for example an amount selected from the group comprising: 1 hour, 2 hours, 3 hours, 4 hours, 5 hours, 6 hours, 7 hours, 8 hours, 9 hours, 10 hours and 11 hours. In yet another example, a direct cleavage event may be deemed to have occurred if a measure of the period (t5–t4) is less than a threshold amount, for example an amount selected from the group comprising: 0.1 hours, 1 hour, 2 hours, 3 hours, 4 hours, 5 hours, 6 hours, 7 hours, 8 hours, 9 hours, 10 hours and 11 hours. In yet another example, a direct cleavage event may be deemed to have occurred if a measure the ratio of a time of cleavage to 3 cells, t3, to a time of cleavage to 4 cells, t4 is less than a threshold amount selected from the group comprising: 0.9, 0.8, 0.7 and 0.6. In some implementations step S5 may involve determining whether any of a number of these time periods is less than its corresponding threshold to identify whether there has been any direct cleavage event.

If it is determined in Step S5 that the current embryo has undergone direct cleavage, processing follows the branch marked Y to step S6 in which the current embryo is attributed a score of 1 and processing then proceeds to step S16. Otherwise, processing follows the branch marked N to step S7.

In step S7 an assessment is made as to whether the duration of a predefined developmental stage is longer than a predefined threshold duration. More generally, in step S7 an assessment is made as to whether an aspect of the embryo's development indicates relatively slow development (which has been found to be associated with relatively low development potential). In this example implementation the duration of the predefined developmental stage is the time taken to reach 3 cells, t3, and the predefined threshold duration is around 43 hours (e.g. 42.91 hours). However, other threshold values could be used in respect of t2, for example the threshold value may be selected from the group comprising: 38 hours, 39 hours, 40 hours, 41 hours, 42 hours, 43 hours, 44 hours, 45 hours, 46 hours, 47 hours and 48 hours.

In some other example implementations different time periods may be used to identify whether there has been slow development. For example, slow development may be deemed to have occurred if a measure of t2 is less than a threshold amount, for example an amount selected from the group comprising: 27 hours, 28 hours, 29 hours, 30 hours, 31 hours, 32 hours, 33 hours, 34 hours and 35 hours. In yet another example, slow development may be deemed to have occurred if a measure of t4 is less than a threshold amount, for example an amount selected from the group comprising: 41 hours, 42 hours, 43 hours, 44 hours, 45 hours, 46 hours, 47 hours, 47 hours, 48 hours, 49 hours and 50 hours. In yet another example, slow development may be deemed to have occurred if a measure of t5 is less than a threshold amount, for example an amount selected from the group comprising: 55 hours, 56 hours, 57 hours, 58 hours, 59 hours, 60 hours, 61 hours, 62 hours and 63 hours. In some implementations step S7 may involve determining whether any of a number of these times are greater than corresponding threshold values to identify whether there has been slow development in respect of any of the time periods.

If it is determined in Step S7 that the current embryo has undergone slow development, processing follows the branch marked Y to step S8 in which the current embryo is attributed a score of 2 and processing then proceeds to step S16. Otherwise, processing follows the branch marked N to step S9.

Steps S9 and S11 in effect operate together to determine if the relative duration of a first predefined developmental stage for the embryo with respect to a second predefined developmental stage for the embryo is inside or outside a predefined range. More generally, these steps combine to assess whether aspects of the embryo's development indicate irregular development in terms of the relative durations of two developmental stages as compared to embryos associated with good developmental potential. In this example implementation the assessment is made in two stages, namely by determining if the relative duration of the first stage to the second stage is below a lower limit for the range in step S9 and determining if the relative duration of the first stage to the second stage is above an upper limit for the range in step s11.

Thus, in step S9 an assessment is made as to whether the relative duration of a first predefined developmental stage for the embryo with respect to a second predefined developmental stage for the embryo is below a predefined limit. In this example implementation the first predefined developmental stage is from cleavage to 3 cells, t3, to cleavage to five cells, t5, (i.e. cc3a) and the second predefined developmental stage is the stage from cleavage to 2 cells, t2, to cleavage to five cells, t5, (i.e. cc2a plus cc3a). Thus a measure of the relative duration used in this example is (t5–t3)/(t5–t2) (equivalent to cc3a/(cc2a+cc3a)). A lower limit for this relative duration in this specific implementation is around 0.34 hours. However, other lower limit values could be used for this parameter, for example, 0.1; 0.2; 0.3; 0.4 or 0.5. In some other example implementations different relative durations may be used to identify whether there has been irregular development and some examples for this are discussed further below.

If it is determined in Step S9 that the current embryo has undergone irregular development because the determined relative duration is below the lower limit, processing follows the branch marked Y to step S10 in which the current embryo is attributed a score of 3 and processing then proceeds to step S16. Otherwise, processing follows the branch marked N to step S11.

In step S11 an assessment is made as to whether the relative duration of a first predefined developmental stage for the embryo with respect to a second predefined developmental stage for the embryo is above a predefined limit. In this example implementation the first and second developmental stages are the same as used in step S9 and the upper limit for this relative duration in this specific implementation is around 0.58 hours. However, other upper limit values could be used for this parameter, for example, 0.6, 0.7, 0.8, or 0.9. As already noted above, in some other example implementations other relative durations may be used to identify whether there has been irregular development and some examples for this are discussed further below.

If it is determined in Step S11 that the current embryo has undergone irregular development because the determined relative duration for the relevant development stages is above the upper limit, processing follows the branch marked Y to step S12 in which the current embryo is attributed a score of 4 and processing then proceeds to step S16. Otherwise, processing follows the branch marked N to step S13.

Thus, and as already discussed above, it will be appreciated the combination of steps S9 and S11 in effect provide a determination of whether the relative duration of a first predefined developmental stage for the embryo with respect to a second predefined developmental stage for the embryo is within a predefined range (in which case the processing of FIG. 5 will for the relevant embryo reach step S13) or outside the range, in which case the embryo will be attributed a score of 3 or 4, depending on whether it is below or above the range. In this particular example implementation the relative duration corresponds with (t5−t3)/(t5−t2), and the predefined range is from around 0.34 to 0.58. However, other ranges may be used, for example the range may be selected from the group comprising: 0.1 to 0.9, 0.2 to 0.8, 0.3 to 0.7, 0.4 to 0.6 and 0.5 to 0.6. In yet other examples, different first and second predefined development stages may be used for establishing whether an embryo displays irregular development in steps corresponding to steps S9 and S13. For example, other parameters and ranges that could be used include:

(t3−t2)/(t5−t2)—with a range of: 0.1 to 0.9, 0.1 to 0.8, 0.2 to 0.7, 0.3 to 0.6 or 0.4 to 0.5

(t3−t2)/(t5−t3)—with a range of: 0.05 to 10, 0.1 to 9, 0.15 to 8, 0.2 to 7, 0.25 to 6, 0.3 to 7, 0.35 to 6, 0.4 to 5, 0.45 to 4, 0.5 to 3, 0.6 to 2 or 0.75 to 1

(t5−t3)/t5—with a range of: more than 0.1, more than 0.2 and more than 0.3

(t4−t3)/(t3−t2))—with a range of more than 0.1, less than 0.2, less than 0.3, less than 0.4 or less than 0.5

(t8−t5)/(t5−t3)—with a range of: less than 0.1, less than 0.15, or less than 0.2

((t3−t2)+(t5−t4))/(t8−t4)—with a range of: more than 0.3, more than 0.4, more than 0.5, more than 0.6, more than 0.7 or more than 0.8

(t8−t5)/(t8−t4)—with a range of: more than 0.3, more than 0.4, more than 0.5, more than 0.6, more than 0.7, more than 0.8, more than 0.9 or more than 0.97

(t3−tPNf)/(t4−tPNf) (or t3/t4)—with a range of: more than 0.35, more than 0.45, more than 0.55, more than 0.65, more than 0.75, more than 0.85, more than 0.95

(t4−t3)/(t4−t2)—with a range of: less than 0.3, less than 0.4, less than 0.5, less than 0.6 or less than 0.7

(t8−t5)/(t8−t2)—with a range of: less than 0.2, less than 0.3, less than 0.4, less than 0.5 and less than 0.6.

It will be noted that some of the ranges listed above are bound only at one end (i.e. some ranges are specified as being a value more than X). In this case, the processing of FIG. 5 may be modified to avoid one or other of step S9 or S11 depending on whether the range is more than a given limit or less than a given limit. Alternatively, an arbitrary extreme value could be set for the relevant limit, such as 0 hours or 999 hours.

It will be appreciated that for all the different ratios of durations for various developmental events (which individually may comprise the sum of 27 amendments, such as for the parameter ((t3−t2)+(t5−t4))/(t8−t4)), what is significant is an indication of the relevant ratio. While this may be calculated as set out above, it but could equally be determined as an "inverse" of these ratios. In this respect it will be appreciated that an indication of a value for A/B is also an indication of a value for B/A.

In step S13 an assessment is made as to whether or not the current embryo developed to a predefined number of cells within a predefined time. In this particular example implementation, step S13 is based on determining whether or not the current embryo failed to reach 8 cells within 66 hours. However, different parameters may be used for this aspect of the processing of FIG. 5 in accordance with other example limitations. For example, instead of 66 hours, the assessment may be based on a different time period, for example a time period selected from the group comprising: 64 hours, 65 hours, 66 hours, 67 hours, 68 hours, 69 hours, 70 hours, 71 hours and 72 hours.

If it is determined in Step S13 that the current embryo failed to reach the requisite number of cells within the relevant time, processing follows the branch marked N to step S14 in which the current embryo is attributed a score of 4 and processing then proceeds to step S16. Otherwise, processing follows the branch marked Y to step S15.

In step S15 the current embryo is attributed a score of 5 and processing proceeds to step S16.

As noted above, in step S16 it is determined whether there are any more embryos to consider from the plurality of embryos being ranked, and if so processing follows the branch marked Y back to step S2 where the processing described above is repeated for the next embryo to be selected. If, on the other hand, there are no more embryos to be considered (i.e. all the plurality of embryos to be ranked have been attributed a score), processing follows the branch marked N to step S17.

In Step S17 the plurality of embryos are ranked relative to one another according to their respective scores. Basically, a higher score is taken to be indicative of a greater development potential. One or more embryos may then be selected from the plurality of embryos which have been ranked for implantation/transfer to a patient based on their ranking. For example, higher ranked embryos may be selected for implantation/transfer to a patient preferentially over embryos with a lower ranking (lower score). In this regard it will be appreciated the specific numerical scores attributed to each embryo (i.e. 0, 1, 2, . . . 5) are not significant. Other values could equally be used. Furthermore, the scoring could be based on a low score indicating good development potential, in which case step S4 of the processing of FIG. 5 would be associated with a higher score than step S6, which will in turn be associated with a higher score than step S8, and so on. Indeed, the scores need not be numerical. For example, embryos may be associated with a score A in step S4, a score B in step S6, and so on to a score E in step D15, and the ranking may be based on identifying embryos associated with the earliest letter in the alphabet as being of relatively low developmental potential.

Thus, the processing of FIG. 5 represents a method for ranking a plurality of embryos according to their development potential in accordance with an embodiment of the invention. This involves establishing whether or not various development stages meet various criteria as discussed above. In particular, the embryos are assessed for direct cleavage (step S5), slow development (step S7) and irregularity (steps S9 and S13 combined). These particular characteristics, and their relative significance to establishing an overall ranking in accordance with the process described above, have been found by the inventors to provide a model for ranking embryos from a cohort to identify those which are most likely to successfully implant, and subsequently leads to a live birth. Furthermore, the inventors have found the approach to be relatively insensitive to characteristics associated with the embryo's development conditions, such as the nature of the fertilisation methods used (ICSI or classical IVF) and the nature of the incubation atmosphere (e.g. low oxygen or ambient oxygen).

To demonstrate the ability of the processing of FIG. 5 to successfully rank embryos according to their development potential, the model may be applied to historical data for embryos for which there is known implantation data (i.e. KID embryos) to establish how well the model predicts the known outcomes for KID embryos. The inventors have done this for around 3,275 KID embryos. This set of 3,275 embryos was taken from a database of information relating to around 17,000 KID embryos. The embryos from the database of 17,000 KID embryos which were not included in the reduced set of 3,275 embryos used to test the model were those for which the quality of annotations for the relevant developmental events was considered unreliable, those for which the patient was over 40 years in age, those that were not relating to day three transfers (since this particular parameters and values used for this specific example of the model are selected to rank embryos for day three transfer), and those associated with pre-implantation genetic screening. The remaining 3,275 KID embryos comprised embryos that could be divided into four main environmental groups, namely (i) classic IVF fertilisation and low oxygen incubation atmosphere, (ii) classic IVF fertilisation and ambient oxygen incubation atmosphere, (iii) ICSI fertilisation and low oxygen atmosphere, and (iv) ICSI fertilisation and ambient oxygen atmosphere. The data for the 3,275 embryos come from 23 different clinics, with 21 clinics contributing data for at least 10 KID embryos, and 9 of these contributing data for at least 100 KID embryos.

The processing of FIG. 5 was applied to each of the 3,275 KID embryos. The results of this, for example in terms of how many embryos were attributed the different scores may be represented by a classification tree for the model, such as represented in FIG. 6.

Figure 6:
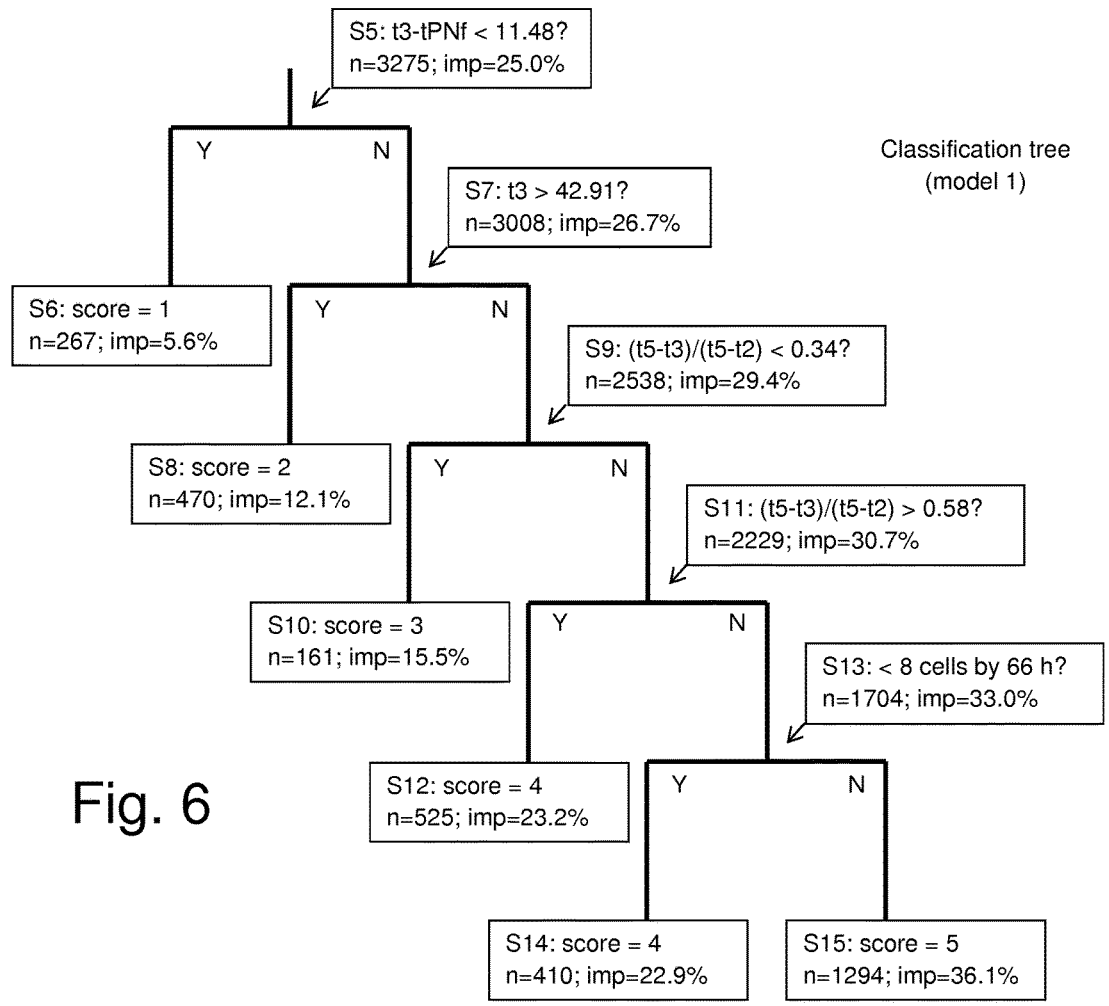
FIG. 6 is a classification tree diagram schematically representing the application of the model of FIG. 5 to 3,275 embryos having known implantation data (KID embryos)

Thus, FIG. 6 is a classification tree representing the application of the model of FIG. 5 to the 3,275 KID embryos. Each branch node (where a classification decision is made) and end/leaf node (where a score is attributed) is identified in FIG. 6 by the corresponding step of the processing of FIG. 5 to which the node relates. Each node is also associated with an indication of the number of embryos (n) that reached that node of the tree and the implantation success of those embryos (imp). Thus the tree starts at step S5 with a population of 3,275 embryos of which 25.0% successfully implanted. The processing of step S5 splits the 3,275 embryos into embryos showing direct cleavage (267 embryos of which 5.6% successfully implanted) and embryos not showing direct cleavage (3008 embryos of which 26.6% successfully implanted). The processing of step S7 then splits the 3,008 embryos from Step S5 into embryos showing slow development (470 embryos of which 12.1% successfully implanted) and embryos not showing slow development (2,538 embryos of which 29.4% successfully implanted). The processing of step S9 then splits the 2,538 embryos from Step S7 into 161 embryos of which 15.5% successfully implanted and 2,229 embryos of which 30.7% successfully implanted). It may be noted that not all embryos are classified in this step (i.e. 161+2,229<2,538). This is because there are some embryos for which it was not possible to apply the classification criterion, e.g. because the relevant timings were not identifiable in the time lapse data. These may be referred to as impute data and they are discounted from further consideration in the application of the model of FIG. 5 to KID embryos for validation purposes as represented in the classification tree of FIG. 6 (i.e. they are not given a score). If there are embryos which cannot be classified in a practical application of the model to a cohort of embryos from a patient, conventional embryologist input may instead be used to assist with ranking these embryos. More generally, it will be recognised that in any event is to be expected that ranking in accordance with the embodiments described herein will typically be used to assist an embryologist make a final ranking decision, and rankings obtained in accordance with embodiments of the invention might not be taken to be definitive without additional embryologist input.

Figure 7:
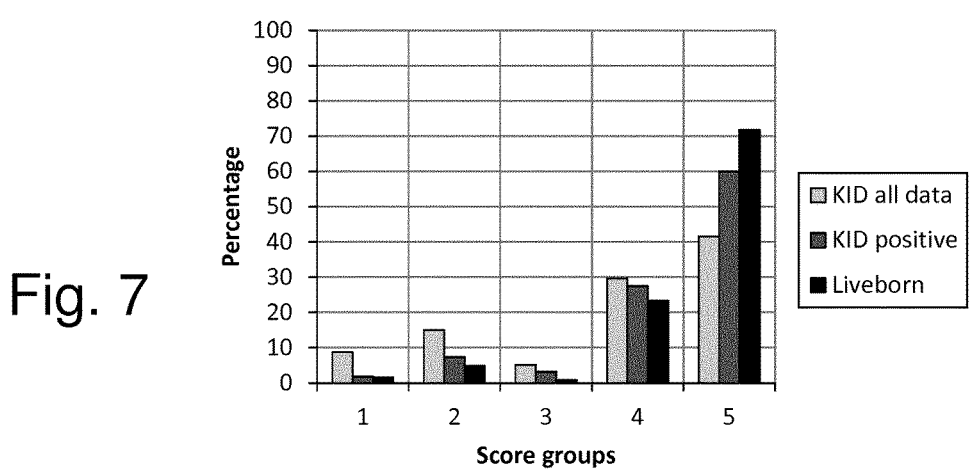
FIG. 7 is a bar chart representing the distribution of various ones of the 3,275 KID embryos associated with the classification tree FIG. 6 among different scores established in accordance with the method of claim 5.

As can be seen from the classification tree of FIG. 6, the application of the model of FIG. 5 to the KID embryos ranks 1294 embryos with a score of 5, and these embryos have an implantation success of 36.1%. This is around 50% higher than the implantation success of the population as a whole, which demonstrates the strength of the model in being able to identify embryos of relatively high quality/development potential from within a plurality of embryos to be ranked. It can also be seen that a total of 935 embryos are attributed a score 4, the breakdown being 410 embryos in step S14 with an implantation success of 22.9% and 525 embryos in step S12 with an implantation success of 23.2%. It is because the embryos reaching step S12 and the embryos reaching step S14 are statistically found to have comparable implantation success rates that both these groups are attributed the same score. The result of applying the model of FIG. 5 to the 3,275 KID embryos used for validation is also represented in FIG. 7. This is a bar chart showing the percentage distribution of the 3,275 KID embryos associated with the classification tree of FIG. 6 among the different scores (identified by the legend "KID all data") and also the percentage distribution of the embryos associated with the classification tree of FIG. 6 which successfully implanted (identified by the legend "KID positive"). Also shown in FIG. 7 is a percentage distribution of a population of embryos known to have resulted in a live birth among scores determined for these embryos in accordance with the model represented in FIGS. 5 and 6 (identified by the legend "Liveborn").

The population of embryos associated with the liveborn data in FIG. 7 do not simply correspond with all of the 3,275 KID embryos which resulted a live birth. This is because live birth data for all these 3,275 KID embryos is not available. This is because once a patient becomes pregnant is not always the case that the IVF clinic where she was treated will be provided with information regarding the final outcome of the pregnancy. Of the 3,275 KID embryos associated with the classification tree of FIG. 6 only around 180 are known to have resulted in a live birth. It is to be expected that many other implanting embryos also resulted in a live birth, but the data on these embryos is simply not available. Thus, the live birth data represented in FIG. 7 correspond with the 180 or so of the 3,275 embryos for which there is live birth data, and an additional 120 or so other embryos which there is live birth data.

FIG. 7 demonstrates how the assessment of development potential in accordance with embodiments of the invention helps to identify embryos having good development potential. For example, it is clear the distributions of embryos associated with good development potential (i.e. "KID positive" and "liveborn" embryos) are skewed to higher scores than population as a whole.

It will be appreciated there are various modifications to the approach of FIG. 5 that can be adopted in accordance with different embodiments. For example, whereas FIG. 5 represents a generally iterative approach in which the embryos are considered and scored in turn, in other implementations the embryos may be scored in parallel, or at least partially in parallel. For example, rather than iterating through steps S2 to S16 for each embryo in turn, in other implementations of the individual steps of the ranking procedure may be performed for a plurality of embryos before moving onto the next step of the ranking procedure. For example, a step corresponding to step S3 may be undertaken for all embryos before the processing moves on to a step corresponding to step S5 in which an assessment as to whether the embryos are to be deemed to have undergone direct cleavage may be performed for all embryos that were not ranked with a score of 0 in the step corresponding to step S3.

Furthermore, in some implementations there may be no step corresponding to S3. That is to say, in some implementations there may not be an assessment as to whether an embryo should be ranked based on the appearance or not of two pro-nuclei. In this case, the processing may the overall similar to that represented in FIG. 5, but with without steps corresponding to steps S3 and S4. Similarly, there may be no steps corresponding with steps S13 and S14 in some examples.

Furthermore, and as already mentioned, different parameters and different threshold values can be used for the various steps of the method. What is significant for certain embodiments of the invention is that the model takes account of direct cleavage, slowness in development (in particular early development), and irregularity in development (by assessing the ratio of two characters associated with different development stages of the embryos) when ranking embryos according to their development potential. There are many different parameters that are indicative of these characteristics, such as the different examples given above. The specific parameters and associated threshold values may vary from implementation to implementation. For example, whilst the above approach has been found to provide a model which is universally applicable, it may be that a specific clinic wishes to develop its own model based on these approaches, and in this case may find that other parameters and/or threshold values provide for optimised discrimination of embryonic development potential for embryos cultured at that clinic. In any event, the relevant parameters and values may be established from a statistical analysis of KID embryos associated with the relevant development conditions. For example, in the case of seeking to establish a universally applicable model, an analysis of how different parameters and associated threshold values performed in ranking the embryos as compared to the known outcomes for the 3,275 KID embryos discussed above is what identified the specific parameters and values for those parameters used in the specific example implementation represented by the classification tree of FIG. 6.

As already mentioned, embodiments of the invention are directed to ranking embryos in a manner which takes account of three aspects of embryo development, namely whether or not the embryos undergo direct cleavage, whether or not the embryos display relatively slow development, and whether or not the embryos display relatively irregular development. Whether or not an embryo displays any of these characteristics may be established from morphokinetic/morphological data associated with the embryo's development. In the example implementation associated with the classification tree of FIG. 6 the assessment of direct cleavage is based on the parameter (t3−tPNf), the assessment of relatively slow development is based on the parameter t3, and the assessment of relatively irregular development is based on the parameter (t5−t3)/(t5−t2). Threshold values for each parameter in this particular example implementation are adopted as previously discussed and as set out in FIG. 6. However, as noted above there are various other parameters and corresponding thresholds that may equally be used to assess the above-identified three development characteristics (direct cleavage, slow development, irregular development) for ranking embryos in accordance with other implementations.

Figure 8:
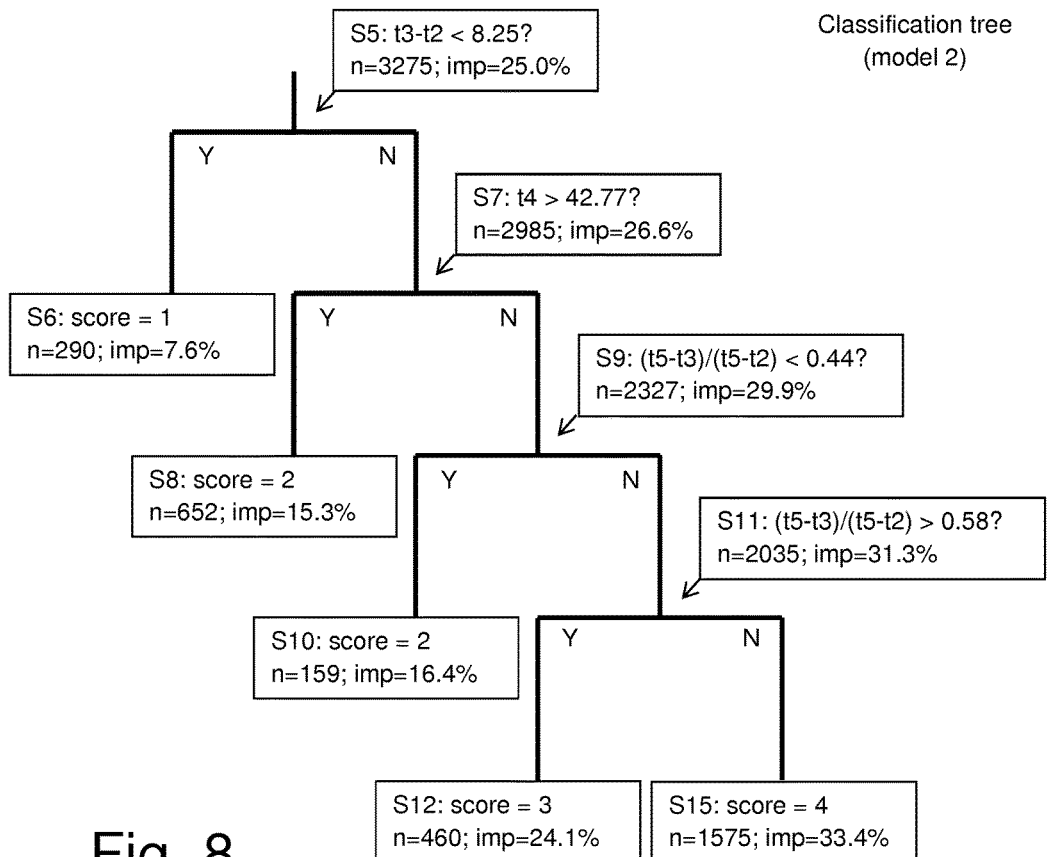
FIGS. 8, 10 and 12 are classification trees schematically representing the application of other models to the 3,275 KID embryos in accordance with other embodiments of the invention.
Figure 9:
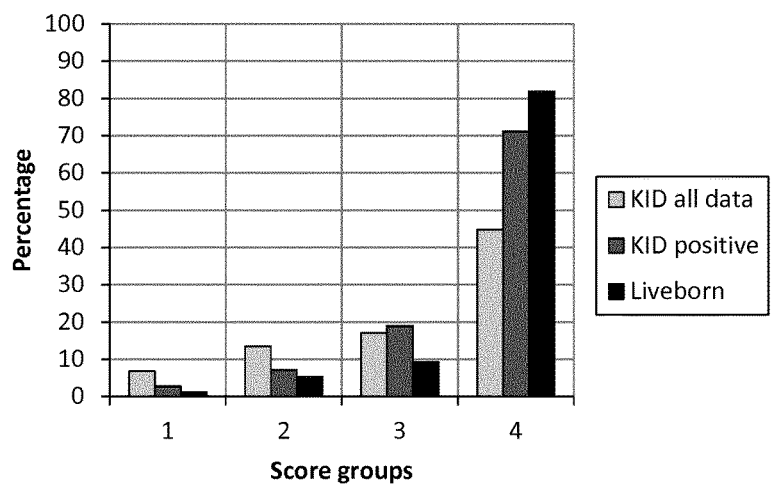
FIGS. 9, 11 and 13 are bar charts representing the distribution of various ones of the 3,275 KID embryos among the different scores established in accordance with the models represented by the classification trees in FIGS. 8, 10 and 12 respectively.
Figure 10:
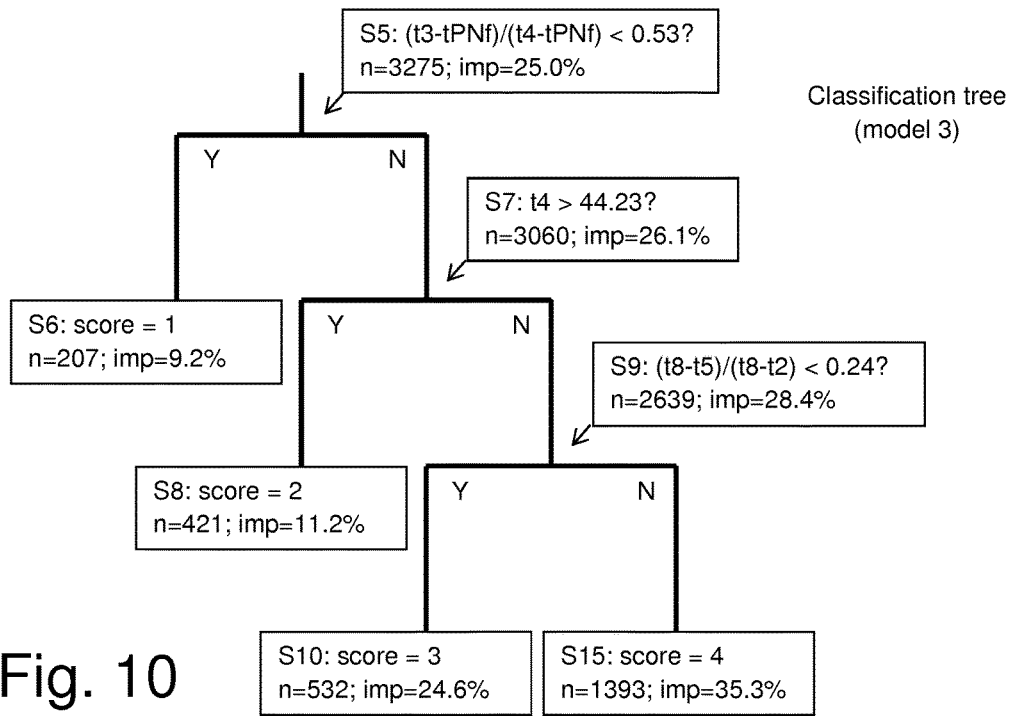
Figure 11:
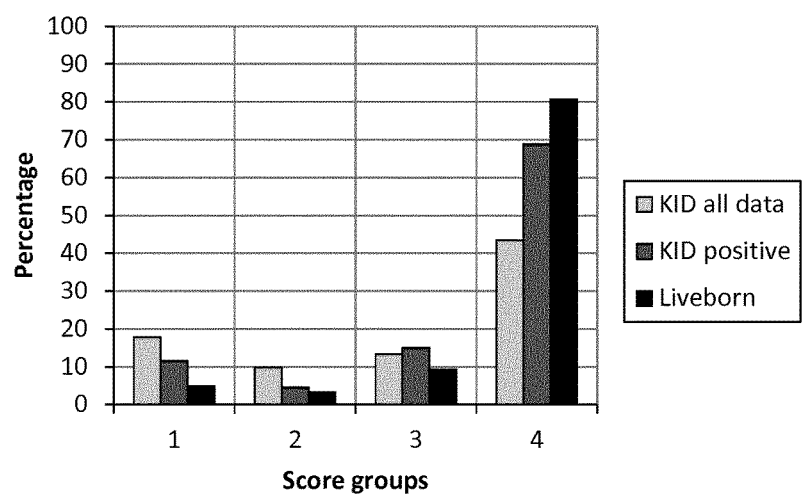
Figure 12:
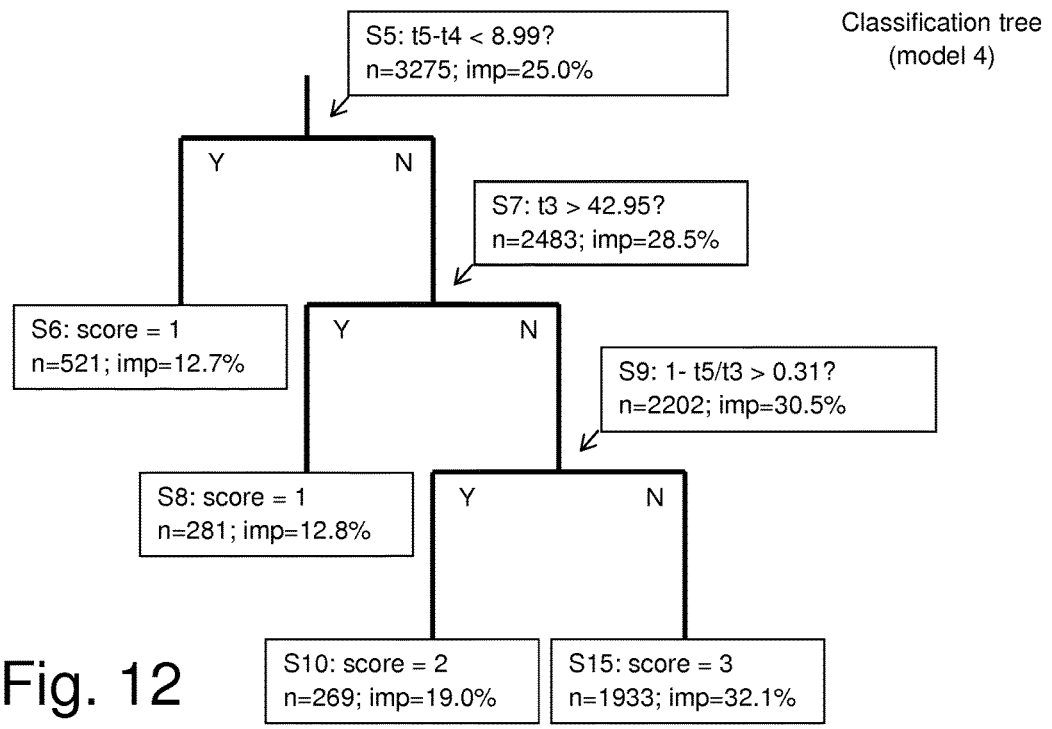
Figure 13:
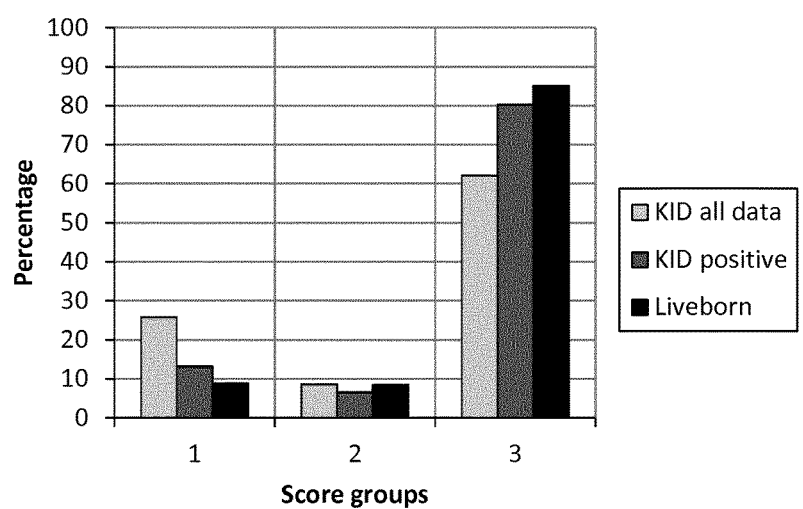

Thus FIGS. 8, 10 and 12 are similar to, and will be understood from, FIG. 6, but show classification trees representing different models based on different parameters and/or threshold values for assessing whether embryos are deemed to be associated with direct cleavage, slow development and/or irregular development. FIGS. 9, 11 and 13 are corresponding bar charts which are similar to, and will be understood from, FIG. 7 for the respective classification trees represented in FIGS. 8, 10 and 12. Again these show how the distributions of embryos associated with good development potential determined in accordance with embodiments of the invention are skewed to higher scores than the population as a whole.

In each of FIGS. 8, 10 and 12 the nodes of the classification tree are identified by the step of the method of FIG. 5 which is most closely associated with the node. However, the models represented FIGS. 8, 10 and 12 do not include all the steps corresponding to the processing of the method FIG. 5 and so there is not a direct correspondence between all nodes in the classification trees of FIGS. 8, 10 and 12 and the classification tree of FIG. 6.

For example, in accordance with the ranking model represented in FIG. 8, there is no step corresponding to step S13 in the method of FIG. 5. That is to say, the ranking of the embryos in accordance with the model of FIG. 8 does not involve a step based on determining whether the embryo has reached a given stage of development within a given time. Consequently, there is one fewer decision node in the classification tree, and the maximum score for the ranking model is consequently less (i.e. 4 instead of 5). However, it will be appreciated the specific numerical ranking obtained in accordance with any given model is for ranking the relative development potential of embryos according to that model. The numerical score is not intended to be an "absolute" ranking for comparison with embryos ranked with different models. That is to say, a score of 5 in the model represented by FIG. 6 is interpreted as a higher ranking than a score of 4 in the model represented by FIG. 6, but it should not be interpreted as necessarily indicating a higher ranking than a score of 4 in the model represented by FIG. 8.

Furthermore, there is no step corresponding to step S11 of the model represented in FIG. 6 in the models represented in FIGS. 10 and 12. This is because the assessment of (ir)regular development in FIG. 6 is based on whether the parameter (t5−t3)/(t5−t2) falls inside or outside a range defined by a lower limit instep S11 and an upper limit in step S13, but the assessment of (ir)regular development in the model of FIG. 10 is based on an assessment of whether (t8−t5)/(t8−2) falls inside or outside the range which is bound only at one end.

For each model the relative scores associated with each leaf node are based on the respective implantation success for the embryos reaching that leaf node. For example, in the model of FIG. 12 the KID embryos reaching the steps marked as corresponding to step S6 (i.e. classified as having undergone direct cleavage) and S8 (i.e. Classified as not having undergone direct cleavage, but displaying slow development) both have comparable implantation likelihoods, and so are attributed the same score.

As can be seen from the model is represented in FIGS. 6, 8, 10 and 12, despite being based on different specific parameters and threshold values for assessing embryos for direct cleavage, slow development and irregular development, the models are all nonetheless able to rank embryos according to the implantation success. For each model the embryos attributed the highest score are associated with implantation likelihoods of around 32% to 36%, which represents a significant improvement over the implantation likelihood for the population of KID embryos taken as a whole, which is 25%. That is to say, the approach of ranking embryos based on the above-identify three characteristics is able to identify those with a higher likelihood of implantation than those with a lower likelihood of implantation.

FIGS. 14 to 17 are classification tree diagrams that are similar to, and will be understood from, FIG. 6. The classification trees of FIGS. 14 to 18 are based on the same model as the classification tree of FIG. 6 (e.g. in terms of the specific parameters and thresholds used to assess for direct cleavage, slow and irregular development), but show the results of applying the model to different subpopulations of the 3,275 KID embryos.

Figure 14:
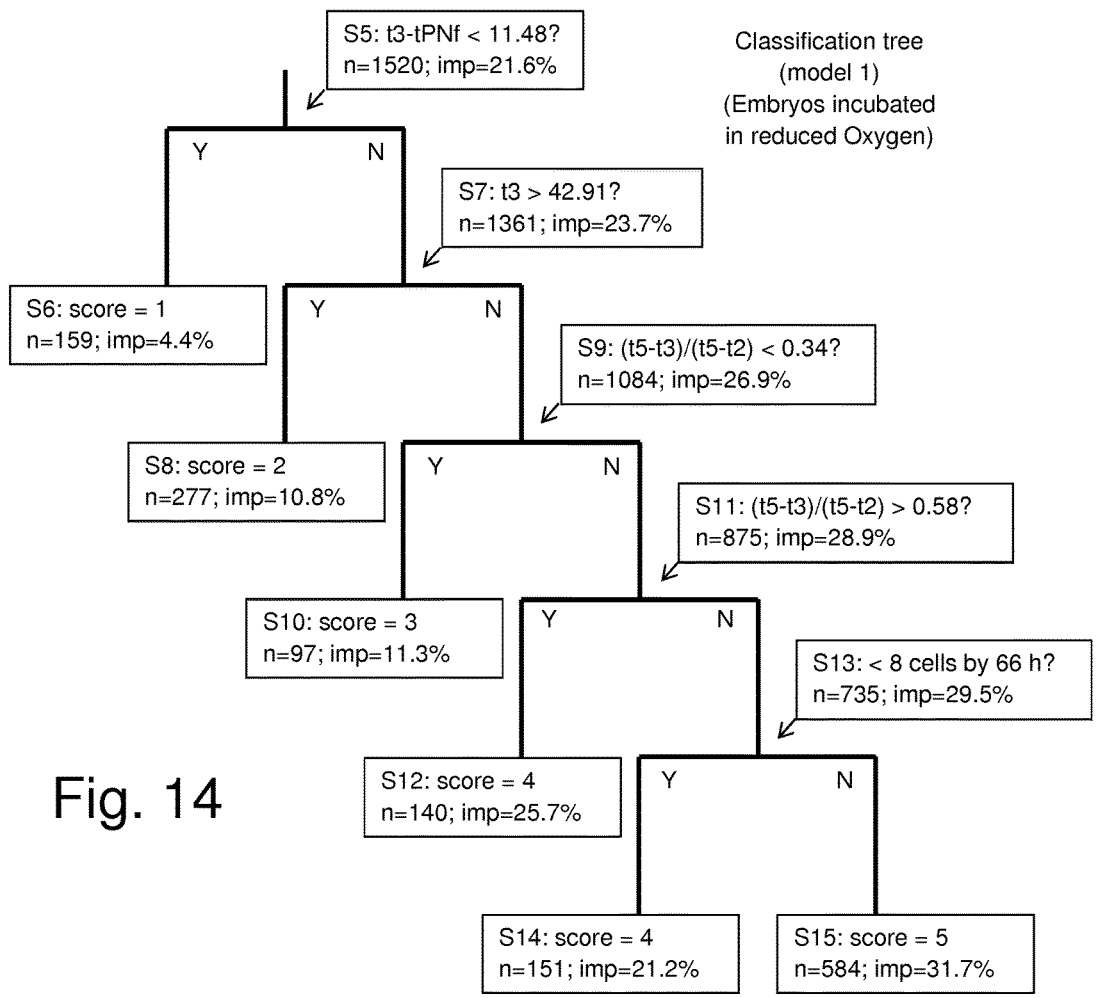
FIGS. 14 to 17 are classification trees schematically representing the application of the same mode to different subpopulations of the 3,275 KID embryos in accordance with embodiments of the invention.
Figure 15:
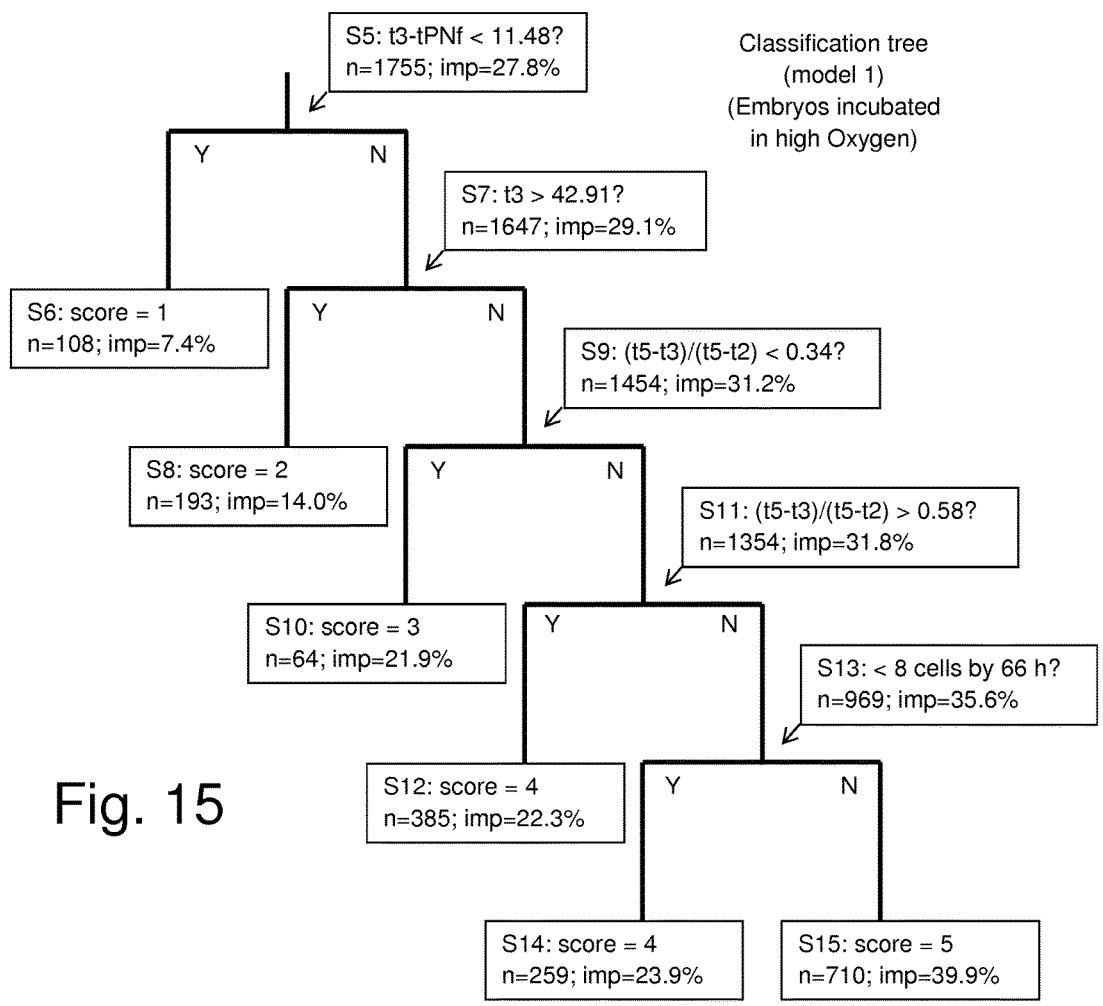

FIG. 14 shows the result of applying the model to the subset of the 3,275 KID embryos incubated in a reduced oxygen atmosphere and FIG. 15 shows the result of applying the model to the subset of the 3,275 KID embryos incubated in an ambient oxygen atmosphere. It can be seen the results from applying the model to embryos incubated in reduced and ambient oxygen atmospheres are comparable, which demonstrates the approach is able to rank embryos with little sensitivity as to whether the embryos are incubated in reduced or ambient oxygen conditions, and this demonstrates the universality of approaches in accordance with embodiments of the invention.

Figure 16:
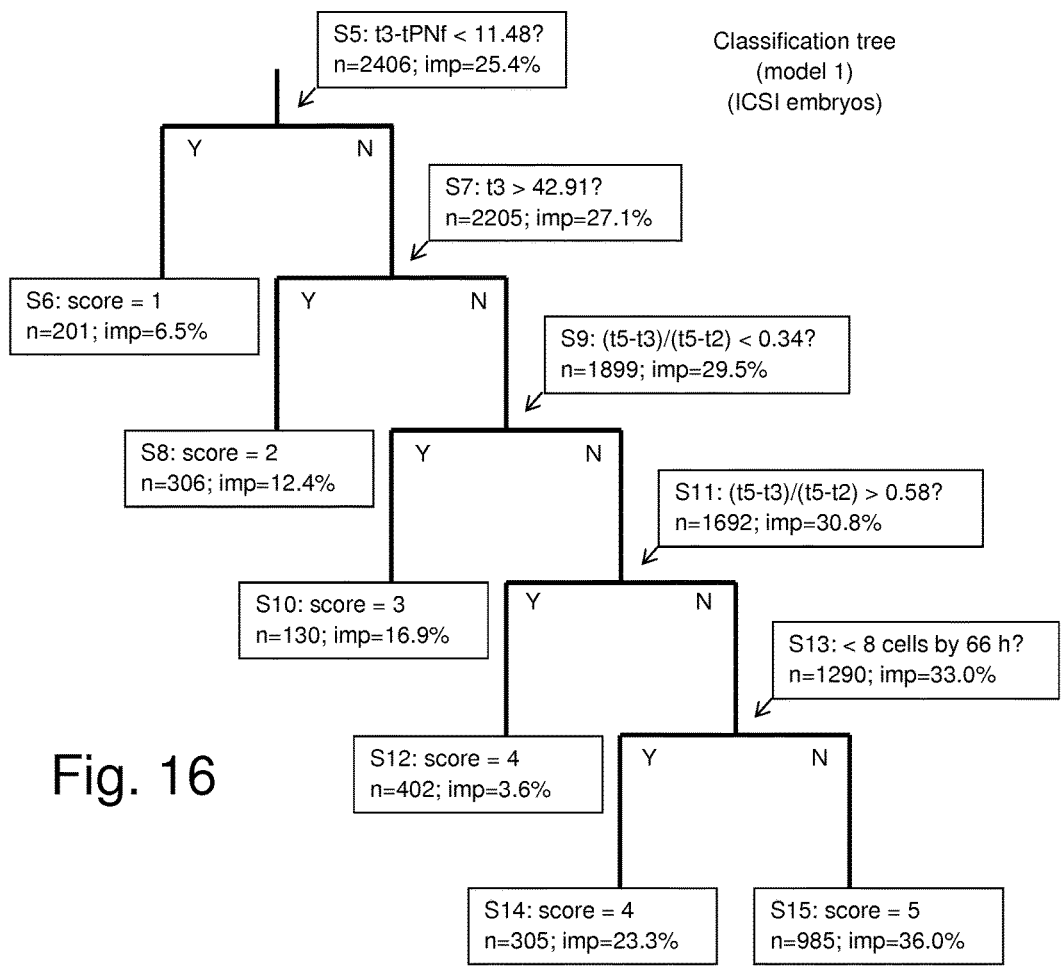
Figure 17:
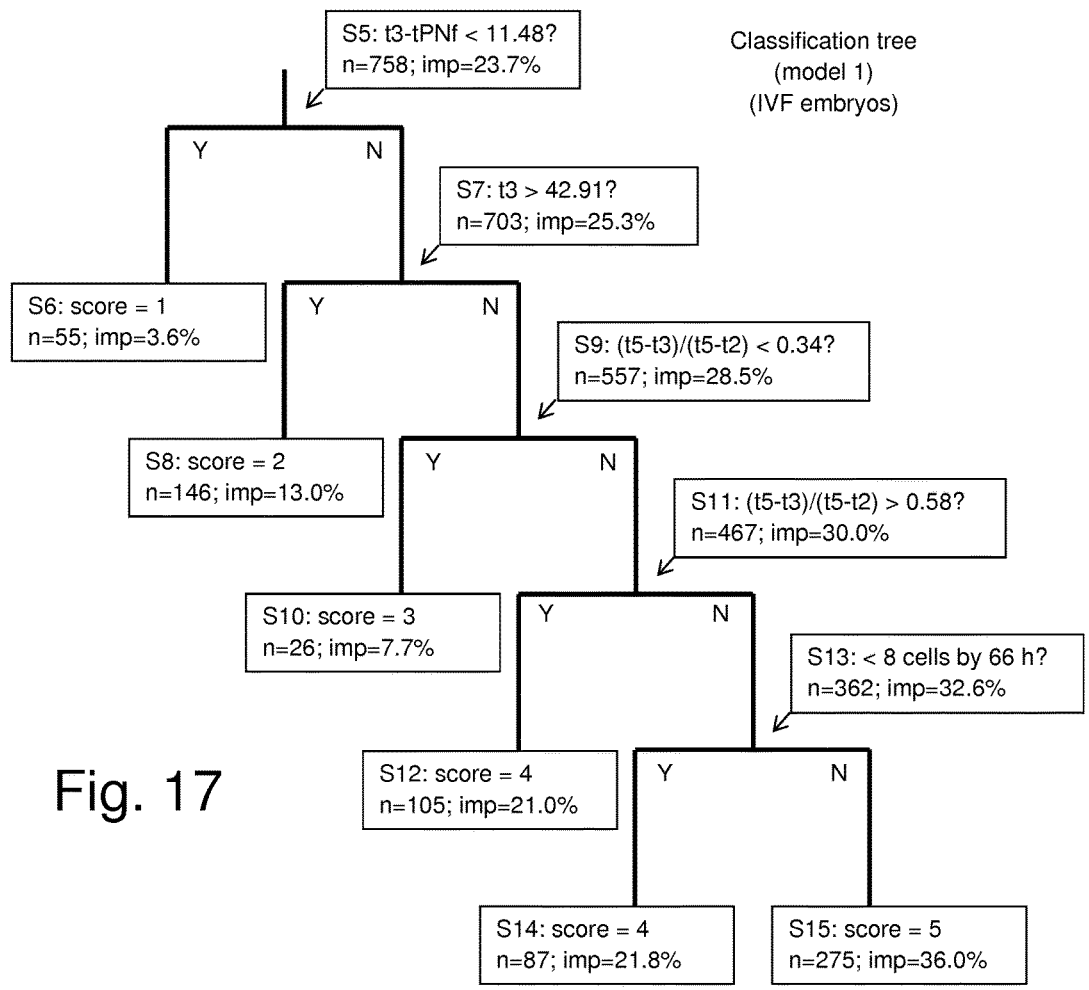
Figure 18:
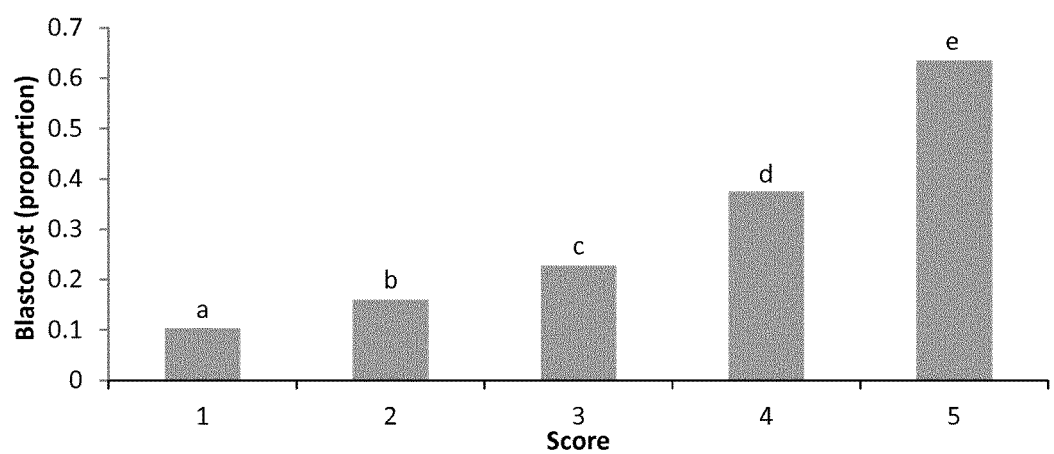
FIG. 18 represents for an analysis of 10,316 embryos for which it is known whether or not the embryos developed to the blastocyst stage by 120 hours after fertilization the proportion of embryos that did develop to the blastocyst stage by 120 hours after fertilization for each of the different scores established for each of the embryos in accordance with the model represented in FIG. 6.

FIG. 16 shows the result of applying the model to the subset of the 3,275 KID embryos fertilized by ICSI and FIG. 17 shows the result of applying the model to the subset of the 3,275 KID embryos fertilized by classic IVF. It can be seen the results from applying the model to ICSI embryos and IVF embryos are comparable, which demonstrates the approach is able to rank embryos with little sensitivity as to whether the embryos are fertilized by ICSI or IVF, and this further demonstrates the universality of approaches in accordance with embodiments of the invention.

It will be appreciated that in addition to assessing embryos for direct cleavage, slowness in development and irregularity when establishing their ranking, another aspect of certain embodiments of the invention is in recognising which of these characteristics should contribute more to a low ranking. In particular, it has been identified that direct cleavage is a stronger indicator of poor development potential than slow development, which in turn is a stronger indicator of poor development than irregular development. Consequently, in accordance with certain embodiments, embryos displaying direct cleavage are ranked lower than embryos not displaying direct cleavage regardless of whether the embryos meet the other criteria. That is to say, of the three criteria: direct cleavage, slowness and irregularity, the determination regarding direct cleavage has a greater impact on an embryo's ranking relative to the other embryos than the determination regarding slowness, and the determination regarding slowness in turn has a great impact on an embryo's ranking relative to the other embryos then the determination regarding irregularity.

The various classification trees for discussed above for KID embryos demonstrate how approaches for ranking a plurality of embryos in accordance with embodiments of the invention can help identify those embryos having the greatest development potential (best quality). This has primarily been shown in the context of development potential measured by likelihood of implantation. However, and as already noted, this is only one example measurement for embryos' development potential and the principal described herein can equally be used for ranking embryos based other measures of development potential, for example the likelihood of reaching a blastocyst stage and/or the likelihood of an implanted embryo developing to a live birth and/or the likelihood of an implanted embryo developing to a stage associated with a heartbeat and/or the likelihood of a patient to whom the embryo is transferred becoming pregnant.

It will be appreciated the stepwise/classification tree approach discussed above is merely one algorithmic approach for ranking embryos on this basis and other algorithmic approaches can in effect give rise to the same ranking scheme. For example, rather than classify embryos using a decision tree, such as represent in the approach of FIGS. 5 and 6, to identify rankings for the embryos, all embryos may be assessed for all three characteristics (direct cleavage, slowness, irregularity) and a cumulative score obtained based on the outcome of the assessment regarding each characteristic. For example, embryos not displaying direct cleavage may be attributed a score of 100 and embryos displaying direct cleavage may be attributed a score of 0 for this score component. Embryos not displaying slowness may be attributed a score of 10 and embryos displaying slowness may be attributed a score of 0 for this score component. Embryos not displaying irregularity may be attributed a score of 1 and embryos displaying irregularity may be attributed a score of 0 for this score component. Thus, an embryo which displays direct cleavage, slowness and irregularity will have a cumulative score of zero, while an embryo which does not display direct cleavage, slowness or irregularity, will have a cumulative score of 111 (maximum). Based on this approach, the embryos would be ranked in an order corresponding to that of the approach of FIG. 6 (except with more refined ranking of embryos within some of the score categories associated with FIG. 5).

Thus there has been described a method of ranking embryos to indicate their development potential. The method comprises: obtaining values for a plurality of characteristics relating to the morphological development of the embryos during an observation period; determining for respective ones of the embryos whether or not the embryo has undergone a direct cleavage event, and ranking the embryos determined to have undergone a direct cleavage event with a ranking that indicates a lower development potential than for the embryos not determined to have undergone a direct cleavage event; and for the embryos not determined to have undergone a direct cleavage event, determining whether or not a duration of a predefined developmental stage for the embryo exceeds a predefined threshold duration, and ranking embryos for which the duration of the predefined developmental stage is determined to exceed the predefined threshold duration with a ranking that indicates a lower development potential than for the embryos for which the duration of the predefined developmental stage is not determined to exceed the predefined threshold duration; and for the embryos for which the duration of the predefined developmental stage is not determined to exceed the predefined threshold duration, determining whether or not the relative durations of two predefined developmental stages for the embryo is outside a predefined range, and ranking embryos for which the relative durations of two predefined developmental stages for the embryo is outside a predefined range with a ranking that indicates a lower development potential than for the embryos for which the relative durations of two predefined developmental stages for the embryo is not outside the predefined range.

In some respects some example embodiments provide a method of ranking embryos to indicate their development potential; the method comprising: obtaining values for a plurality of characteristics relating to the morphological development of the embryos during an observation period; determining for respective ones of the embryos a measure of whether or not the embryo underwent a direct cleavage event; determining for respective ones of the embryos a measure of whether or not a duration of a predefined developmental stage for the embryo was longer than a predefined threshold duration; determining for respective ones of the embryos a measure of whether or not the relative durations of two predefined developmental stages for the embryo is outside a predefined range; and ranking the embryos in such a way that a determination that an embryo underwent a direct cleavage event contributes more to a ranking that indicates a relative low development potential than does a determination that the duration of the predefined developmental stage for the embryo was longer than the predefined threshold duration, and wherein a determination that the predefined developmental stage for the embryo was longer than the predefined threshold duration contributes more to a ranking that indicates a relative low development potential than does a determination that the relative durations of two predefined developmental stages for the embryo is outside the predefined range.

In some respects some other example embodiments provide a method of establishing a score to indicate a development potential for an embryo; comprising: obtaining values for a plurality of characteristics relating to the morphological development of the embryo during an observation period; determining, as a first score component, a measure of whether or not the embryo underwent a direct cleavage event; determining, as a second score component, a measure of whether or not a duration of a predefined developmental stage for the embryo was longer than a predefined threshold duration; determining, as a third score component, an indication of whether or not the relative durations of two predefined developmental stages for the embryo is outside a predefined range; and establishing a score to indicate a development potential for the embryo by taking account of the first score component, the second score component and the third score component in such a way that the first score component has a greater impact on the score than the second or third score components, and the second score component has a greater impact on the score than the third score component.

Thus, and as discussed above, methods in accordance with the principles described herein may be used to establish a score to indicate a development potential for an embryo. The examples set out above have mainly focused on providing an indication of the likelihood of successful implantation based on known implantation data for a sample of embryos. However, as has already explained, the method is also applicable for establishing scores relating to other development potential characteristics for embryos, for example the likelihood of an embryo developing to the blastocyst stage.

In this regard, the model represent in FIG. 6 has been applied to a dataset comprising 10,316 embryos from 2413 patients/37 clinics incubated for five days and for which it is known whether or not the embryos developed to the blastocyst stage by 120 hours. In effect, this corresponds with using what might be termed "known blastocyst data" instead of "known implantation data" used for some of the other results described herein to establish the ability of the model to establish an indicator of developments potential.

The dataset of 10,316 embryos was completely independent from the dataset on which the model of FIG. 6 was developed. This dataset of 10,316 embryos contained kinetic information of the relevant development parameters annotated in accordance with the guidelines proposed in the paper "Proposed guidelines on the nomenclature and annotation of dynamic human embryo monitoring by a time-lapse user group" by Ciray et al—Hum. reprod. 2014; 29; 2650-2660 [1]. The kinetic information up to day three post-fertilization was used to score the embryos in accordance with the algorithm represented by FIG. 6, thereby assigning each embryo to one of the score groups (1, 2, 3, 4 or 5).

The number of embryos allocated score 1 was 2024 (of which 1911 were traditional IVF fertilised; 93 were ICSI fertilised; and the fertilisation method for 20 was unknown). The number of embryos allocated score 2 was 1443 (of which 1281 were traditional IVF fertilised; 143 were ICSI fertilised; and the fertilisation method for 19 was unknown). The number of embryos allocated score 3 was 656 (of which 629 were traditional IVF fertilised; 16 were ICSI fertilised; and the fertilisation method for 11 was unknown). The number of embryos allocated score 4 was 1734 (of which 1546 were traditional IVF fertilised; 147 were ICSI fertilised; and the fertilisation method for 41 was unknown). The number of embryos allocated score 5 was 4459 (of which 3991 were traditional IVF fertilised; 417 were ICSI fertilised; and the fertilisation method for 51 was unknown). Thus, for the total of 10,316 embryos, 9358 were traditional IVF fertilised; 816 were ICSI fertilised; and the fertilisation method for 142 was unknown.

To evaluate the capability of the model algorithm as a blastocyst prediction tool, the proportion of the embryos which developed to the blastocyst stage (blastocyst formation) by 120 hours post-fertilisation was determined for each of the five score groups. The results of this are presented in FIG. 18. This clearly shows an increasing proportion of embryos associated with each score developed to blastocyst stage with increasing score (for example, over 60% of embryos associated with score 5 developed to blastocyst stage as compared to around 10% of embryos associated with score 1 developing to blastocyst stage). This further demonstrates the ability of the above-describe methods to establish an indicator of an embryo development potential (this case the likelihood of developing to the blastocyst stage).

To test for differences in the fraction of embryos that formed blastocysts between the score groups to which they were assigned, a generalized linear mixed-effects regression (GLMER, with a Bernoulli error distribution) was performed in respect of likelihood of blastocyst formation for the different score groups, fertilization method (ICSI or IVF) and incubations oxygen level (reduced or ambient) as explanatory variables (fixed effects). All interaction terms between score group, fertilization method and oxygen level were included to verify whether blastocyst formation fractions in the score groups was influenced by these incubation characteristics. To account for patient and clinic variability, this information was included as a random intercept, in which patients were nested within clinics. Stepwise backwards elimination was used for model reduction, starting with the full model, including all interactions of the parameters. An inclusion criterion of $p<0.01$ was used in the elimination procedure. The final model included the main effects of score and fertilization method (ICSI/IVF).

This analysis demonstrated 1) a significant difference in the likelihood of blastocyst formation between the score groups, with increasing score is associated with increased likelihood of blastocyst formation, and 2) the blastocyst proportion for IVF was higher than ICSI. This illustrates the principal described herein can be used based on the information available up to day three post-fertilisation to predict the likelihood of blastocyst formation. As none of the interaction terms were found significant, the general pattern of blastocyst proportions in the score groups can be concluded to be the same between IVF and ICSI. The fact that the blastocyst proportion was higher in IVF than in ICSI may be explained by the general clinical practice that ICSI is especially used for the more difficult cases.

Further particular and preferred aspects of the present invention are set out in the accompanying independent and dependent claims. It will be appreciated that features of the dependent claims may be combined with features of the independent claims in combinations other than those explicitly set out in the claims.

REFERENCES

[1] Ciray et al, "Proposed guidelines on the nomenclature and annotation of dynamic human embryo monitoring by a time-lapse user group", Hum. reprod. 2014; 29; 2650-2660.

What is claimed is:

1. A method of ranking embryos to indicate their development potential; the method comprising:
   obtaining values for a plurality of characteristics relating to the morphological development of the embryos during an observation period;
   using the values to determine for respective ones of the embryos a measure of whether or not the embryo has undergone a direct cleavage event, and ranking the embryos determined to have undergone a direct cleavage event with a ranking that indicates a lower development potential than for the embryos not determined to have undergone a direct cleavage event including determining whether a first parameter associated with the embryo's development is less than a first threshold amount, and if so, determining that the embryo has undergone a direct cleavage event; and
   for the embryos not determined to have undergone a direct cleavage event, using the values to determine whether or not a measure of a duration of a predefined developmental stage for the embryo exceeds a predefined threshold duration, and ranking embryos for which the duration of the predefined developmental stage is determined to exceed the predefined threshold duration with a ranking that indicates a lower development potential than for the embryos for which the duration of the predefined developmental stage is not determined to exceed the predefined threshold duration; and
   for the embryos for which the duration of the predefined developmental stage is not determined to exceed the predefined threshold duration, using the values to determine whether or not a measure of a relative duration of a first predefined developmental stage for the embryo with respect to a second predefined developmental stage for the embryo is outside a predefined range, and ranking embryos for which the relative duration is outside the predefined range with a ranking that indicates a lower development potential than for the embryos for which the relative duration of is not outside the predefined range, wherein:

(i) the first parameter is a measure of the time period between pro-nuclei fading, tPNf, and the time of cleavage to 3 cells, t3, and wherein the first threshold amount is selected from the group comprising: 5 hours, 6 hours, 7 hours, 8 hours, 9 hours, 10 hours, 11 hours, 12 hours, 13 hours and 14 hours; or
   (ii) the first parameter is a measure the time period between the time of cleavage to 2 cells, t2, and the time of cleavage to 3 cells, t3, and the first threshold amount is selected from the group comprising: 1 hour, 2 hours, 3 hours, 4 hours, 5 hours, 6 hours, 7 hours, 8 hours, 9 hours, 10 hours and 11 hours; or
   (iii) the first parameter is a measure of the time period between the time of cleavage to 4 cells, t4, and the time of cleavage to 5 cells, t5, and wherein the first threshold amount is selected from the group comprising: 0.1 hours, 1 hour, 2 hours, 3 hours, 4 hours, 5 hours, 6 hours, 7 hours, 8 hours, 9 hours, 10 hours and 11 hours; or
   (iv) the first parameter is a measure of a ratio of a time of cleavage to 3 cells, t3, to a time of cleavage to 4 cells, t4, and wherein the first threshold amount is selected from the group comprising: 0.9, 0.8, 0.7 and 0.6.

2. The method according to claim 1, wherein determining whether or not a measure of a duration of a predefined developmental stage for the embryo exceeds a predefined threshold duration comprises:
   (i) determining if a measure of a time of cleavage to 2 cells, t2, exceeds a time selected from the group comprising: 27 hours, 28 hours, 29 hours, 30 hours, 31 hours, 32 hours, 33 hours, 34 hours and 35 hours; or
   (ii) determining if a measure of a time of cleavage to 3 cells, t3, exceeds a time selected from the group comprising: 38 hours, 39 hours, 40 hours, 41 hours, 42 hours, 43 hours, 44 hours, 45 hours, 46 hours, 47 hours and 48 hours; or
   (iii) determining if a measure of a time of cleavage to 4 cells, t4, exceeds a time selected from the group comprising: 41 hours, 42 hours, 43 hours, 44 hours, 45 hours, 46 hours, 47 hours, 47 hours, 48 hours, 49 hours and 50 hours; or
   (iv) determining if a measure of a time of cleavage to 5 cells, t5, exceeds a time selected from the group comprising: 55 hours, 56 hours, 57 hours, 58 hours, 59 hours, 60 hours, 61 hours, 62 hours and 63 hours.

3. The method according to claim 1, wherein in determining whether or not a measure of the relative duration of a first predefined developmental stage for the embryo with respect to a second predefined developmental stage for the embryo is outside a predefined range,
   (i) the first predefined developmental stage is a measure of the time period between the time of cleavage to 3 cells, t3, and the time of cleavage to 5 cells, t5, and the second predefined developmental stage is a measure of the time period between the time of cleavage to 2 cells, t2, and the time of cleavage to 5 cells, t5, such that the relative duration is a measure of $(t5-t3)/(t5-t2)$, and wherein the predefined range is selected from the group comprising: 0.1 to 0.9, 0.2 to 0.8, 0.3 to 0.7, 0.4 to 0.6 and 0.5 to 0.6;
   or
   (ii) the first predefined developmental stage is a measure of the time period between the time of cleavage to 2 cells, t2, and the time of cleavage to 3 cells, t3, and the second predefined developmental stage is a measure of the time period between the time of cleavage to 2 cells, t2, and the time of cleavage to 5 cells, t5, such that the relative duration is a measure of (t3−t2)/(t5−t2), and wherein the predefined range is selected from the group comprising: 0.1 to 0.9, 0.1 to 0.8, 0.2 to 0.7, 0.3 to 0.6 or 0.4 to 0.5;

or (iii) the first predefined developmental stage is a measure of the time period between the time of cleavage to 2 cells, t2, and the time of cleavage to 3 cells, t3, and the second predefined developmental stage is a measure of the time period between the time of cleavage to 3 cells, t3, and the time of cleavage to 5 cells, t5, such that the relative duration is a measure of (t3−t2)/(t5−t3), and wherein the predefined range is selected from the group comprising: 0.05 to 10, 0.1 to 9, 0.15 to 8, 0.2 to 7, 0.25 to 6, 0.3 to 7, 0.35 to 6, 0.4 to 5, 0.45 to 4, 0.5 to 3, 0.6 to 2 and 0.75 to 1;

or (iv) the first predefined developmental stage is a measure of the time period between the time of cleavage to 3 cells, t3, and the time of cleavage to 5 cells, t5, and the second predefined developmental stage is a measure of the time of cleavage to 5 cells, t5, such that the relative duration is a measure of (t5−t3)/t5), and wherein the predefined range is selected from the group comprising: more than 0.1, more than 0.2 and more than 0.3;

or (v) the first predefined developmental stage is a measure of the time period between the time of cleavage to 3 cells, t3, and the time of cleavage to 4 cells, t4, and the second predefined developmental stage is a measure of the time period between the time of cleavage to 2 cells, t2, and the time of cleavage to 3 cells, t3, such that the relative duration is a measure of (t4−t3)/(t3−t2), and wherein the predefined range is selected from the group comprising: less than 0.1, less than 0.2, less than 0.3, less than 0.4 and less than 0.5;

or (vi) the first predefined developmental stage is a measure of the time period between the time of cleavage to 5 cells, t5, and the time of cleavage to 8 cells, t8, and the second predefined developmental stage is a measure of the time period between the time of cleavage to 3 cells, t3, and the time of cleavage to 5 cells, t5, such that the relative duration is a measure of (t8−t5)/(t5−t3), and wherein the predefined range is selected from the group comprising: less than 0.1, less than 0.15, and less than 0.2;

or (vii) the first predefined developmental stage is a measure of the combined time periods between the time of cleavage to 2 cells, t2, and the time of cleavage to 3 cells, t3, and between the time of cleavage to 4 cells, t4, and the time of cleavage to 5 cells, t5, and the second predefined developmental stage is a measure of the time period between the time of cleavage to 4 cells, t4, and the time of cleavage to 8 cells, t8, such that the relative duration is a measure of ((t3−t2)+(t5−t4))/(t8−t4), and wherein the predefined range is selected from the group comprising: more than 0.3, more than 0.4, more than 0.5, more than 0.6, more than 0.7 and more than 0.8;

or (viii) the first predefined developmental stage is a measure of the time period between the time of cleavage to 5 cells, t5, and the time of cleavage to 8 cells, t8, and the second predefined developmental stage is a measure of the time period between the time of cleavage to 4 cells, t4, and the time of cleavage to 8 cells, t8, such that the relative duration is a measure of (t8−t5)/(t8−t4), and wherein the predefined range is selected from the group comprising: more than 0.3, more than 0.4, more than 0.5, more than 0.6, more than 0.7, more than 0.8, more than 0.9 and more than 0.97;

or (ix) the first predefined developmental stage is a measure of the time period between pronuclei fading, tPNf, and the time of cleavage to 3 cells, t3, and the second predefined developmental stage is a measure of the time period between pro-nuclei fading, tPNf, and the time of cleavage to 4 cells, t4, such that the relative duration is a measure of (t3−tPNf)/(t4−tPNf), and wherein the predefined range is selected from the group comprising: more than 0.35, more than 0.45, more than 0.55, more than 0.65, more than 0.75, more than 0.85, and more than 0.95;

or (x) the first predefined developmental stage is a measure of the time period between the time of cleavage to 3 cells, t3, and the time of cleavage to 4 cells, t4 and the second predefined developmental stage is a measure of the time period between the time of cleavage to 2 cells, t2, and the time of cleavage to 4 cells, t4, such that the relative duration is a measure of (t4−t3)/(t4−t2), and wherein the predefined range is selected from the group comprising: less than 0.3, less than 0.4, less than 0.5, less than 0.6 and less than 0.7;

or (xi) the first predefined developmental stage is a measure of the time period between the time of cleavage to 5 cells, t5, and the time of cleavage to 8 cells, t8, and the second predefined developmental stage is a measure of the time period between the time of cleavage to 2 cells, t2, and the time of cleavage to 8 cells, t8, such that the relative duration is a measure of (t8−t5)/(t8−t2), and wherein the predefined range is selected from the group comprising: less than 0.2, less than 0.3, less than 0.4, less than 0.5 and less than 0.6.

4. The method according to claim 1, further comprising:
for the embryos for which the relative duration of the first predefined developmental stage with respect to the second predefined developmental stage is outside a predefined range,
determining if the relative duration is above or below the predefined range; and ranking embryos for which the relative duration is outside the predefined range to one side of the predefined range with a ranking that indicates a lower development potential than for the embryos for which the relative duration is outside the predefined range to the other side of the predefined range.

5. The method according to claim 1, further comprising for the embryos determined to have undergone a direct cleavage event, determining whether or not a measure of a duration of a predefined developmental stage for the embryo exceeds a predefined threshold duration, and ranking the embryos determined to have undergone a direct cleavage event and for which the duration of the predefined developmental stage is determined to exceed the predefined threshold duration with a ranking that indicates a lower development potential than for the embryos determined to have undergone a direct cleavage event and for which the duration of the predefined developmental stage is not determined to exceed the predefined threshold duration.

6. The method according to claim 1, further comprising for the embryos determined to have undergone a direct cleavage event, determining whether or not a measure of a relative duration of a first predefined developmental stage for the embryo with respect to a second predefined developmental stage for the embryo is outside a predefined range, and ranking the embryos determined to have undergone a direct cleavage and for which the relative duration is outside the predefined range with a ranking that indicates a lower development potential than for the embryos determined to have undergone a direct cleavage event and for which the relative duration of is not outside the predefined range.

7. The method according to claim 1, further comprising for the embryos not determined to have undergone a direct cleavage event and for which the duration of the predefined developmental stage is determined to exceed the predefined threshold duration, determining whether or not a measure of a relative duration of a first predefined developmental stage for the embryo with respect to a second predefined developmental stage for the embryo is outside a predefined range, and ranking the embryos determined to have undergone a direct cleavage and for which the duration of the predefined developmental stage is determined to exceed the predefined threshold duration and for which the relative duration is outside the predefined range with a ranking that indicates a lower development potential than for the embryos determined to have undergone a direct cleavage event and for which the duration of the predefined developmental stage is determined to exceed the predefined threshold duration and for which the relative duration of is not outside the predefined range.

8. The method according to claim 1, wherein for the embryos for which the relative duration of the first predefined developmental stage with respect to the second predefined developmental stage is determined to be within the predefined range, determining whether or not the respective embryos have developed to a predefined number of cells within a predefined time, and ranking embryos which have not developed to the predefined number of cells in the predefined time with a ranking that indicates a lower development potential than for the embryos determined to have developed to the predefined number of cells in the predefined time.

9. The method according to claim 8, wherein the predefined number of cells is eight cells and the predefined time is selected from the group comprising: 64 hours, 65 hours, 66 hours, 67 hours, 68 hours, 69 hours, 70 hours, 71 hours and 72 hours.

10. The method according to claim 1, wherein the values are obtained by time-lapse microscopy.

11. The method according to claim 1, further comprising outputting an indication representing the rankings for at least some of the embryos relative to one another.

* * * * *